United States Patent [19]

Renzel et al.

[11] 4,333,345

[45] Jun. 8, 1982

[54] DISPLAY OF ULTRASOUND TEST DATA

[75] Inventors: Peter Renzel, Düren; Klaus Kroesen, Bonn, both of Fed. Rep. of Germany

[73] Assignee: Krautkramer-Branson, Inc., Stratford, Conn.

[21] Appl. No.: 199,244

[22] Filed: Oct. 21, 1980

[30] Foreign Application Priority Data

Nov. 9, 1979 [DE] Fed. Rep. of Germany ....... 2945201

[51] Int. Cl.³ ............................................ G01N 29/04
[52] U.S. Cl. ........................................ 73/606; 73/611; 73/620
[58] Field of Search .................. 73/606, 607, 611, 620; 328/185; 340/748

[56] References Cited

U.S. PATENT DOCUMENTS

| | | | |
|---|---|---|---|
| 3,577,007 | 5/1971 | Cross | 328/185 |
| 3,603,981 | 9/1971 | Rollenhagen | 328/181 |
| 4,064,742 | 12/1977 | Pittaro | 73/611 |
| 4,088,028 | 5/1978 | Hildebrandt | 73/611 |

Primary Examiner—Anthony V. Ciarlante
Attorney, Agent, or Firm—Ervin B. Steinberg; Philip J. Feig

[57] ABSTRACT

Display of the results of non-destructive testing with a beam of ultrasonic energy is enhanced by exercising precise control over the horizontal sweep voltage which is applied to the deflection plates of a cathode ray tube on which the test information is displayed. The sweep voltage generator produces a sawtooth waveform which has a precisely selectable slope. The sawtooth voltage waveform slope may be adjusted by selecting the capacitance, which is charged from an adjustable constant current source, and by varying the charging current. A microprocessor, which stores information commensurate with various waveform slopes, will control the adjustment of the sawtooth waveform slope by comparison of the stored information with keyboard entered data corresponding to a desired slope.

12 Claims, 18 Drawing Figures

| | |
|---|---|
| GATE | 1 |
| GATE START | 000.0 MM |
| GATE WIDTH | 060.0 MM |
| GATE THRESHOLD | 12 % |
| COINCIDENCE | YES |
| LED DISPLAY | YES |
| ALARM | YES |
| MAXIMUM VALUE DETECTOR | NO |
| DISPLAY | YES |

DISPLAY OF ULTRASOUND TEST DATA

BACKGROUND OF THE INVENTION (1) Field of the Invention

The present invention relates to non-destructive testing and particularly to the display of the results of the examination of test objects with a beam of ultrasonic energy. More specifically, this invention relates to a computer controlled display which permits comparison of test results with preselected parameters commensurate with a selected examination range within the test object and/or with a threshold level. Accordingly, the general objects of the present invention are to provide novel and improved methods and apparatus of such character.

(2) Description of the Prior Art

This invention generally relates to the presentation of echo signals received from a workpiece being examined by means of a beam of ultrasonic energy. These echo signals are commonly converted to electrical signals and displayed on the screen of the cathode ray tube of an oscilloscope. The oscilloscope will include controls for varying the position and intensity of the electron beam of the CRT. However, prior art oscilloscope display devices have not had the capability of establishing, and subsequently displaying if desired, a "gate" or "window" commensurate with echo signals having at least a predetermined magnitude and/or received at a time commensurate with a reflection from a selected depth range within the body of the workpiece. Thus, it has previously been necessary to perform tedious measurements and calibrations in order to know, with precision, that a particular echo related signal being displayed has emanated from a point within the examination range of interest and/or is greater than a minimum predetermined amplitude

SUMMARY OF THE INVENTION

The present invention overcomes the above-briefly discussed and other deficiencies and disadvantages of the prior art by providing a novel and improved technique for displaying information commensurate with the results of non-destructive testing and apparatus for the use in the practice of such method.

It is thus an object of the invention to provide for the evaluation of echo signals in respect of location and amplitude which are manifest at a predetermined position on the cathode ray tube of a display device.

Apparatus in accordance with a preferred embodiment of the invention includes a microprocessor, with associated data entry keyboard, for computing the desired conditions and particularly the slope of the deflection voltage of a CRT display. The computed information is employed to adjust the deflection voltage so as to cause the display of information bearing signals only during a time commensurate with examination of a zone of interest.

The microprocessor also computes the bounds of a region within the examination zone and generates signals which define in terms of time, the bounds of this zone. These zone boundary signals are processed in such a manner as to alternately display the zone, typically as a horizontal bar, on the CRT screen. This bar may be superimposed on the information bearing signal.

The microprocessor also computes a threshold range for the information bearing signals and, through comparison of this threshold with actual information bearing signal magnitude, may provide an alarm.

BRIEF DESCRIPTION OF THE DRAWING

The present invention may be better understood, and its numerous objects and advantages may become apparent to those skilled in the art, by reference to the accompanying drawing wherein like reference numerals generally refer to like elements in the several FIGURES and in which.

DESCRIPTION OF THE PREFERRED EMBODIMENTS

Figure 1:
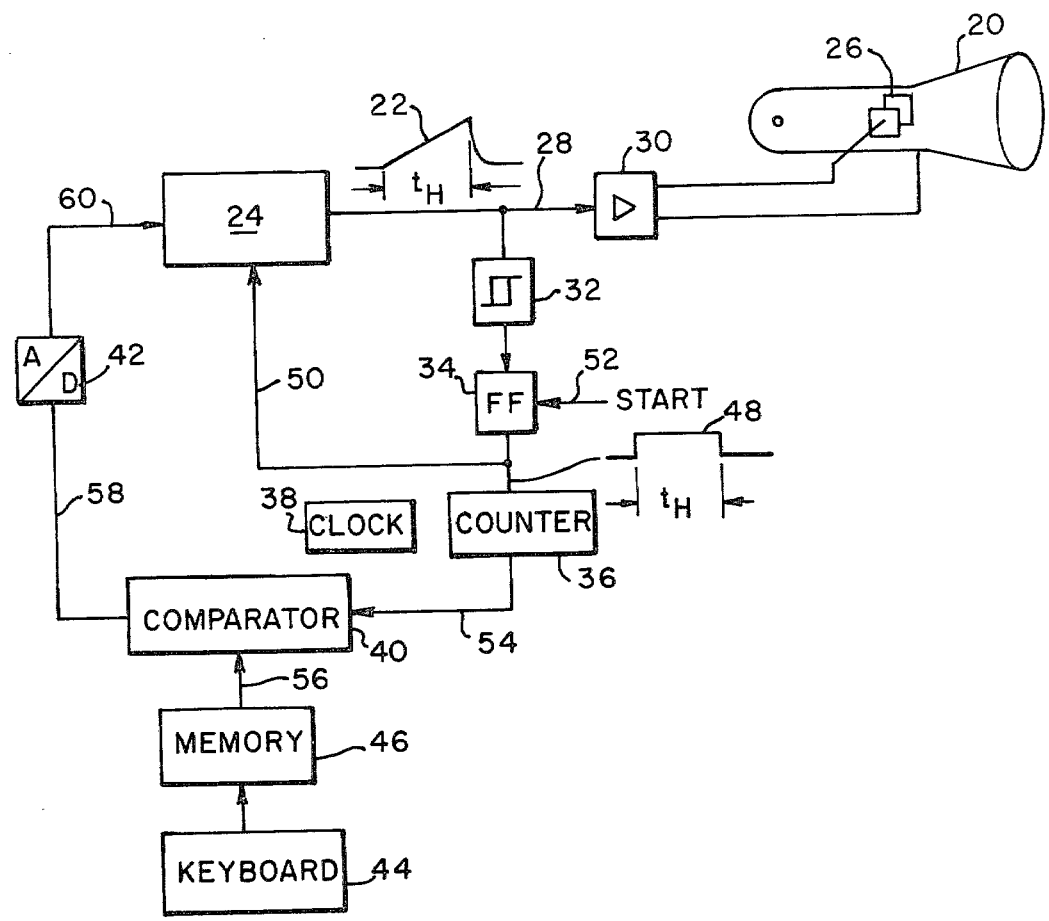
FIG. 1 is a functional block diagram of a display device in accordance with the present invention.

Referring first to FIG. 1, a portion of a display device is depicted by means of a functional block diagram. The display device includes a cathode ray tube 20. A sweep or deflection voltage, the waveform of which is indicated at 22, is generated by a sweep voltage generator 24 and applied to a first pair of oppositely disposed deflection plates 26 in CRT 20 via conductor 28 and amplifier 30. For purposes of the discussion below, the deflection plates 26 will be considered to be the horizontal deflection plates of CRT 20 and generator 24 will produce a sawtooth waveform having a horizontal traversing time $t_H$. The time $t_H$ required for the output of generator 24 to vary between the levels required to cause the electron beam to sweep across all or a predetermined portion of the screen of CRT 20 is precisely controlled and maintained; i.e., the slope of waveform 22 is precisely defined; by the control circuitry shown in FIG. 1. This control circuitry includes a Schmidt trigger 32, a flip-flop circuit 34, a counter 36, a clock pulse generator 38, a comparator 40 and a digital to analog converter 42. The slope of waveform 22 is adjustable, in a manner to be described below, by an operator selected input signal which may be entered via a keyboard 44. The information entered by the operator commensurate with the desired rise time $t_H$ is stored in a first "memory" device 46.

The operation of the apparatus of FIG. 1 will now be described. The flip-flop 34 serves to initiate and terminate the linear portions of the cycles of the output voltage of generator 24 by applying a gating signal, indicated at 48, to generator 24 via conductor 50. The duration of the gate signal 48 is equal to the actual traversing time $t_H$ of the portion of the sawtooth signal provided by generator 24. The gate signal is initiated; i.e., the flip-flop 34 is set, by receipt of an external trigger pulse over conductor 52. This gating signal may, in the manner to be described below, be generated under the control of a microprocessor. The flip-flop 34 will be reset, thereby terminating the gating pulse 48, by an output signal provided by Schmidt trigger 32 when the amplitude of the sawtooth voltage 22 exceeds a preselected threshold of Schmidt trigger 32. The actual duration of the time $t_H$ is measured by converting the gating pulse 48 from flip-flop 34 into a digital signal. This is done by employing gating signal 48 to enable counter 36 whereby the counter will count pulses from clock 38 for as long as the gating signal is present. Accordingly, the final count in counter 36 is commensurate with the actual value of the traversing time $t_H$. This "number" is applied, via conductor 54, to a first input of comparator 40.

As noted above, a desired or set point value of the time $t_H$ may be selected and entered by means of the keyboard 44. When the keys are actuated, in the manner known and customary in the art, a digital code will be generated and this digital signal will be loaded into intermediate memory 46. The digital code can be produced through the use of key switch mechanisms of the type commercially available from Datanetics/Knitter or through the use of a diode matrix. The number loaded into memory 46 is applied, via the output 56 of memory 46, as a second input to comparator 40.

The comparator 40 compares the actual value of the traversing time $t_H$, as indicated by the count stored in counter 36, with the nominal or set-point value of the time $t_H$ as indicated by the number which has been loaded into memory 46. If these two numbers or values differ, a digital signal commensurate with the difference will appear at the output 58 of comparator 40 and this difference or error signal will be delivered to the digital to analog converter 42. The digital to analog converter 42 will, accordingly, apply, via conductor 60, an analog signal commensurate with the difference between the actual and desired times $t_H$ to an input to the sweep voltage generator 24. In the manner to be described below, the sweep voltage generator 24 will vary the slope of its output waveform as a function of the input signal applied thereto from converter 42. The comparison of the actual and nominal values of the traversing times $t_H$ will take place until such time as these values are identical.

Figure 2:
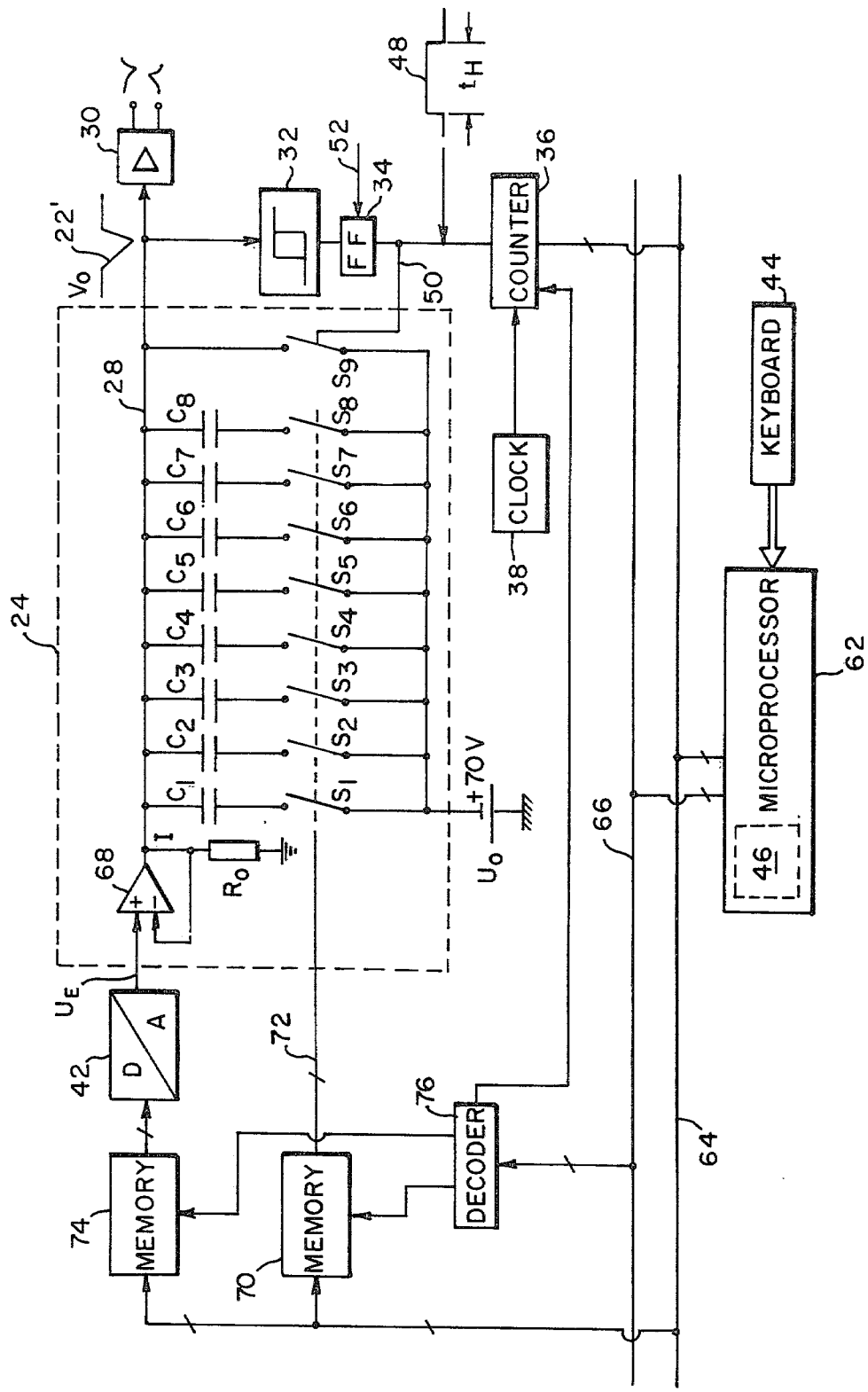
FIG. 2 is a circuit block diagram of a sweep voltage generator in accordance with the present invention and suitable for use in the display device of FIG. 1.

Referring now to FIG. 2, a portion of the circuitry of FIG. 1, and particularly the means by which the slope of generator 24 is controlled, is shown in greater detail. As depicted in FIG. 2, the function of the comparator 40 of FIG. 1 may advantageously be performed in a microprocessor 62 which includes the intermediate memory 46. As will be described in greater detail below, the microprocessor 62 also performs a number of additional monitoring and control tasks. A commercially available microprocessor suitable for use in the practice of the present invention is type Z80 available from Mostek, Inc. and identified as "Microprocessor Device DMK". The digitally coded signal provided by keyboard 44 is delivered to microprocessor 62 and the microprocessor is coupled to the remaining elements of the display device, as required, by means of data bus 64 and control or address bus 66. In the manner known in the art, both the data and address buses will typically be eight-conductor bidirectional buses which respectively transmit and receive binary coded data and control commands. It will also be understood that suitable input/output devices will be interconnected between the microprocessor 62 and the data and address buses; such input/output devices also being available from Mostek, Inc. in integrated circuit form.

The sweep voltage 24 is shown schematically in FIG. 2. Sweep voltage 24 includes an operational amplifier 68 which receives the analog output signal $U_E$ provided by digital to analog converter 42. Sweep voltage generator 42 also comprises a resistor $R_O$ and a plurality of parallel connected capacitors. In the example shown, there are eight capacitors $C_1$ through $C_8$ which may be selectively connected between Sweep voltage generator output conductor or bus 28 and a voltage source $U_O$ by means of respective individually operable switches $S_1$ through $S_8$. The switches $S_1$–$S_8$ are preferably solid state switches of the type to be further described in the discussion of FIG. 3. Each of switches $S_1$–$S_8$ is connected to, and thus responsive to, a separate one of eight outputs of a further storage device 70; the eight output lines of storage device 70 being indicated schematically by a single conductor 72. The sweep voltage 24 includes a further switch $S_9$ which is responsive to the gating signal 48 provided at the output of flip-flop 34. As described above, the gating signal is initiated by the delivery of a trigger pulse to input 52 of flip-flop 34 via conductor 52 thereby initiating "release" of the sawtooth pulse 22. Switch $S_9$ is normally closed, thereby establishing a short circuit across capacitors $C_1$–$C_8$, and is operated to the open state by the gating signal 48. The operational amplifier 68 is connected as a non-inverting amplifier and, in combination with resistor $R_O$, functions as a constant current source. The current I provided by amplifier 68 is a function of the magnitude of the input signal $U_E$ applied thereto from converter 42 and the size of resistor $R_O$.

In operation, when switch $S_9$ is opened by a gating signal appearing at the output of flip-flop 34, any of capacitors $C_1$–$C_8$ which have been connected in the circuit by the closing of their respective series connected switches will be charged by the constant current I from the discharged state; i.e., the state where the voltage source $U_O$ has been applied to both sides of the capacitors via the closed switch $S_9$. The charge on the plates of the capacitors which are connected to the output of amplifier 68 will flow to ground through resistor $R_O$ thereby increasing the potential difference across any capacitor which is connected to source $U_O$ through a closed switch $S_1$–$S_8$. As a consequence, the output 28 of sweep voltage generator 24 will be a linearly decreasing sawtooth voltage having the waveform indicated at 22'. The slope of this linearly decreasing voltage is dependent upon the total capacitance of those of parallel connected capacitors $C_1$–$C_8$ which are connected into the circuit and upon the magnitude of the constant current I. The capacitors $C_1$–$C_8$ represent the coarse setting of the traversing time $t_H$ while the magnitude of the current I, which is dependent on the input voltage $U_E$ to amplifier 68, is a "fine" adjustment of time $t_H$. When the linearly decreasing portion of sawtooth voltage 22' crosses the lower threshold of Schmidt trigger 32 in the negative-going direction, the flip-flop 34 will be reset as described above whereby the gating signal 48 will terminate and switch $S_9$ will automatically return to the normally closed state. The reclosing of switch $S_9$ causes those capacitors which are in the circuit to discharge while the electron beam in CRT 20 returns, during the fly-back portion of the cycle, to its starting point.

During the above-described operation above, the duration of the gating signal 48 at the output of flip-flop 34 has been measured and stored through the combined action of clock pulse generator 38 and counter 36 and the value of this count is transferred to microprocessor 62 via data bus 64. Microprocessor 62 then, pursuant to its stored program, computes the difference between the digital values corresponding to the count in counter 36 and the desired $t_H$ time entered via keyboard 44 and delivers a digital value equal to the difference between these "set-point" and actual values of the traversing time $t_H$ to a further storage device 74. The number loaded into storage device 74 is, by the digital to analog counter 42, converted into the analog input signal $U_E$ which is applied to amplifier 68 to vary the magnitude of the current I and thereby cause a change in the traversing time of the next sawtooth waveform. In actual practice, storage device 74 will receive and store a digital signal commensurate with equality between the actual and set-point values of the time $t_H$ and the "number" in storage device 74 will be incremented or decremented when microprocessor 62 detects an error.

A prerequisite to the "fine" adjustment mentioned above is that the actual value of the time $t_H$ is at least roughly equal to the set-point value at the beginning of the comparison. This preliminary "coarse" setting is obtained by means of the microprocessor selecting a combination of capacitors $C_1$–$C_8$ so that the total capacitance in the sweep voltage generator circuits together with an average control voltage value $U_E$ (initial number to be loaded into storage device 74), which produces a traversing time which lies near the desired nominal value. The microprocessor obtains the appropriate combination of capacitors by consulting a table which correlates the externally supplied setting, i.e., the information entered via keyboard 44; with the appropriate combination of capacitors. Instructions are then generated by microprocessor 62 which will cause the closing of the correct one or more of switches $S_1$–$S_8$. This switch closure instruction is loaded into storage device 70. The clearing and loading of storage devices 70 and 74 and counter 36 is under the control of the output of a decoder 76 which is connected to bus 66 and thus is controlled by the output of microprocessor 62.

The above-mentioned table, which is employed to obtain the "coarse" setting of sweep generator 24, is generated by a suitable program and may be checked for accuracy from time to time in automatic fashion. For example, after the display device has been energized, the microprocessor may select an average value for the voltage $U_E$ and then connect capacitors $C_1$–$C_8$ sequentially into the sweep voltage generator while constructing a table of coarse; i.e., approximate values; for the traversing time $t_H$ of the sawtooth voltage. These values are then temporarily stored. Thereafter, the set-point value of the traversing time entered by means of the keyboard 44 is compared with the temporarily stored "coarse" values and the closest approximate value is chosen by loading a "number" into storage device 70 which will cause the appropriate set of the switches $S_1$–$S_8$ to be closed.

The above-described "coarse" adjustment is followed by the "fine" adjustment previously described. This process may take place cyclically in several stages; i.e., by successive approximation in, for example, eight steps; and may be repeated from time to time so as to insure the long-term constancy of the selected traversing time. Preferably, the desired value of the traversing time $t_H$ is determined as follows: After the coarse adjustment, the microprocessor 62 causes a digital signal to be applied to the input of converter 42 having the hexadecimal value 0 and stores the resulting traversing time $t_{H1}$ which appears at the output of counter 36. The number in counter 36 thus represents the traversing time $t_H$ which occurs for an adjustment current of value 0. Subsequently, the process is repeated for a signal with the hexadecimal value FF=255 and the resulting traversing time $t_{H2}$ is also stored; this value representing the traversing time for the maximum adjustment current I. Using the values $t_{H1}$ and $t_{H2}$ and the pre-selected nominal time $t_H$, the microprocessor 62 then obtains the digital value DW which more closely approximates the desired traversing time $t_H$ on the basis of the following relation:

$$DW = 255(1 - t_H/t_{H1}) - (t_H/t_{H2} - t_H/t_{H1}) \qquad (1)$$

This digital value is transferred, via storage device 74, to converter 42 which generates a voltage $U_E$ that is used to adjust the current I in such a way as to obtain the desired traversing time $t_H$.

The derivation of formula (1) is not a prerequisite to the understanding of the present invention. Nevertheless, the following considerations are offered.

Assuming $t_H = k \cdot C/I$, where k is a constant, C is the capacitance to be charged and I is the constant current set by resistor $R_O$, then if $$I = U_E/R_O \text{ and } U_E = a \cdot DW + b$$

Where a and b are constants, and using the expressions $$a_1 = a/(K \cdot RC), \text{ and } b_1 = b/(K \cdot RC),$$

one obtains, for DW=0:

$$t_{H1} = 1/b_1;\ b_1 = 1/t_{H1}$$

and for DW=FF:

$$t_{H2} = 1/(a_1 FF + 1/t_{H1}); \quad a_1 = 1/FF(1/t_{H2} - 1/t_{H1})$$

When the values of $a_1$ and $b_1$ are substituted in the above equations, formula (1) is obtained.

Figure 3:
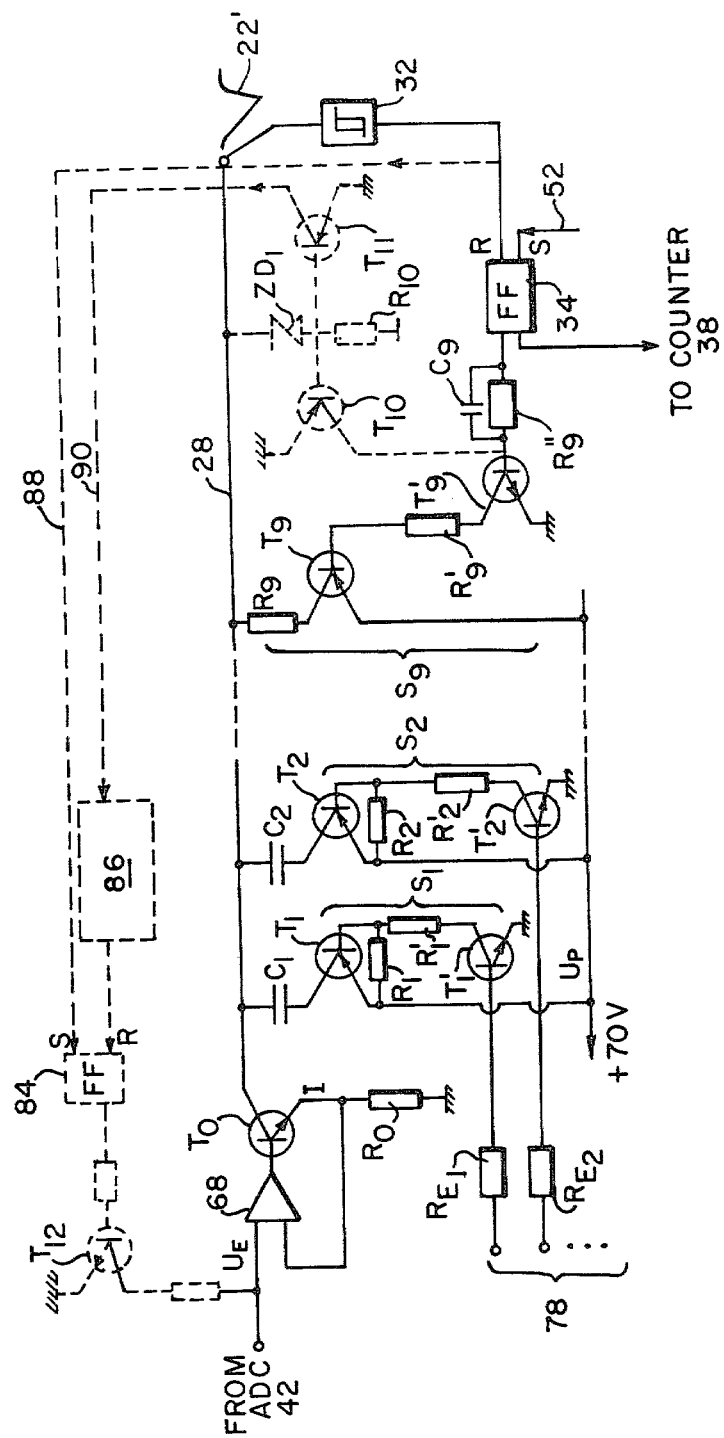
FIG. 3 is an electrical circuit schematic of a portion of the sweep voltage generator of FIG. 2.

Turning now to FIG. 3, a preferred construction of the switches $S_1$–$S_9$, which are functionally represented in FIG. 2, are shown schematically. In FIG. 3, in order to facilitate understanding of the invention, only switches $S_1$, $S_2$ and $S_9$ are shown. Switch $S_1$ is comprised of an amplifier circuit including transistors $T_1$ and $T_1'$ and a voltage divider comprising resistors $R_1$ and $R_1'$. The base of transistor $T_1'$ is connected, via resistor $R_{E1}$, to one of the output terminals of storage device 70; the output of storage device 70 being schematically represented in FIG. 3 by conductor 78. All of switches $S_1$ and $S_8$ are of identical construction and each is connected, in the manner shown, to a first plate of a respective one of capacitors $C_1$–$C_8$. The opposite plate of each of the capacitors is, as previously discussed, connected to the output of operational amplifier 68. Continuing to describe swtich $S_1$, transistor $T_1'$ is normally not conductive and is switched into the conductive state by the appearance of a signal at the output of storage device 70 to which $T_1'$ is connected via resistor $R_{E1}$. When transistor $T_1'$ becomes conductive, it will cause normally non-conductive transistor $T_1$ to switch to the conductive state thereby applying the source voltage $U_O$ to capacitor $C_1$; capacitor $C_1$ being connected directly to the collector of $T_1$. As shown in FIG. 3, operational amplifier 68 is actually coupled to the output bus 28 of sweep voltage generator 24, and thus to capacitors $C_1$–$C_8$, by means of a further transistor $T_o$. Transistor $T_o$ serves only to minimize the effect of the constant current I on operational amplifier 68.

The switch $S_9$, which applies potential $U_O$ to sweep generator output bus 28 when in the closed state, is comprised of a normally conductive transistor $T_9$ and a normally non-conductive transistor $T_9'$, and resistors $R_9$ and $R_9'$. Switch $S_9$, and more precisely the base of transistor $T_9'$, is connected to the output of flip-flop 34 by means of a parallel connection of resistor $R_9''$ and capacitor $C_9$. As previously discussed the set input of flip-flop 34 receives a trigger pulse on conductor 52 while the reset input of flip-flop 34 is connected to the output of Schmidt trigger 32. When flip-flop 34 is set, transistor $T_9'$ will be turned on thereby biasing transistor $T_9$ into the non-conductive state thus removing the short circuit across those of capacitors $C_1$–$C_8$ which are connected into the sweep generator circuit by means of their respective series connected switches $S_1$–$S_8$. When the gating signal supplied by flip-flop 34 is terminated, by the output of Schmidt trigger 32, transistor $T_9'$ returns to its non-conductive state thereby switching transistor $T_9$ back into the conductive state thereby connecting source $U_O$ directly to bus 28.

Figure 4A:
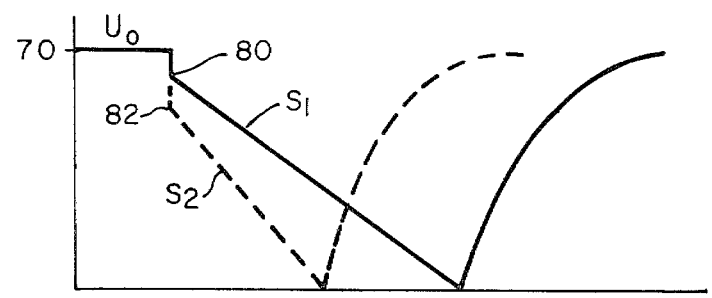
FIGS. 4a and 4b are waveform diagrams which facilitate understanding of the operation of the sweep voltage generator of FIGS. 2 and 3.
Figure 4B:
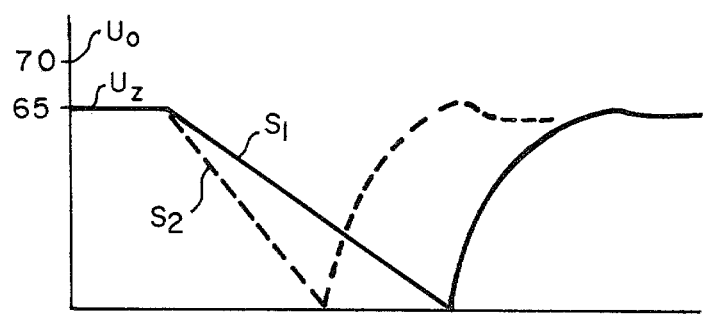

The control circuitry of FIG. 3 preferably, but not necessarily, contains additional elements which have been depicted by means of a broken-line showing. These additional elements, which will be described below, improve the effectiveness of the operation of the circuit but are not essential for operation. These additional elements include a Zener diode $ZD_1$, resistor $R_{10}$ and a further transistor $T_{10}$. The aforementioned elements, in cooperation with switch $S_9$, form a control loop that defines the base potential of the sawtooth waveform 22' which appears on bus 28. Without such a control loop, the base voltages of the sawtooth waveforms of differing slope could differ as a result of different impedances of the switches and particularly of the transistors $T_1$–$T_8$. Thus, referring to FIG. 4a, the base potential of the sawtooth waveform generated when switch $S_1$ only is closed is indicated at 80. The base potential of the sawtooth waveform, which has been shown in broken lines for purposes of comparison, which results for when switch $S_2$ only is closed is indicated at 82. Both of base potentials 80 and 82 are, as a consequence of the circuit impedance, lower than potential $U_o$ and the difference in base potentials 80 and 82 results from different impedances in switches $S_1$ and $S_2$. FIG. 4b illustrates what happens when the circuit comprising Zener diode $ZD_1$ and transistor $T_{10}$ is operative. The Zener diode $ZD_1$ is chosen so that it becomes conductive at a voltage $U_Z$ which is less than the source voltage $U_o$; i.e., in the present example $U_Z$ is 65 volts whereas $U_o$ is 70 volts. The base of transistor $T_{10}$ is connected to the junction of Zener diode $ZD_1$ and current-limiting resistor $R_{10}$. When Zener diode $ZD_1$ conducts, indicating that the voltage on the output bus 28 of sweep voltage generator 24 exceeds the preselected level $U_Z$, transistor $T_{10}$ will switch transistor $T_9'$ into the conductive state thus causing transistor $T_9$ to switch to the non-conductive state and switch $S_9$ to open. When the voltage on bus 28 is lower than the level $U_Z$, switch $S_9$ will function as described above and transistor $T_9$ will be in the conductive state.

FIG. 3 also shows additional control circuitry which includes a transistor $T_{11}$, a flip-flop 84, a monostable multivibrator 86 and a transistor $T_{12}$. It is the function of the components described immediately above to minimize the return time; i.e., the fly-back; of the sawtooth voltage to thereby return the electron beam in CRT 20 to its starting point in the shortest possible time. The return time will be very short if the resistance of resistor $R_9$ is relatively small, for example 50 ohms, thereby permitting the charge on the capacitor or capacitors connected in the sweep voltage generator circuit to be rapidly dissipated and the potential on bus 28 to rapidly return to the value $U_o$ (or $U_z$) after transistor $T_9$ becomes conductive. However, if constant current I was also permitted to flow through transistor $T_9$ during this return period, the total current would be quite high and damage to $T_9$ might result. Accordingly, the constant current I is interrupted at the start of the fly-back; i.e., at the beginning of the trailing portion of the sawtooth waveform. Interruption of the delivery of current I, under the control of operational amplifier 68, is accomplished by passing the output pulse from Schmidt trigger 32, to the set input of flip-flop 84 via conductor 88. The setting of flip-flop 84 will cause normally non-conductive transistor $T_{12}$ to be turned on thereby pulling the input to amplifier 68 substantially to ground potential. The foregoing will result in amplifier 68 providing an output signal which biases transistor $T_o$ to the point where substantially no current will flow through resistor $R_O$. When the Zener diode $ZD_1$ threshold voltage $U_Z$ is exceeded, the voltage drop across resistor $R_{10}$ will be amplified by transistor $T_{11}$ and applied, via conductor 90, to the input of monostable multivibrator 86. The multivibrator 86 will then provide a short reset pulse which is applied to the reset input of flip-flop 84. The resetting of flip-flop 84 will result in transistor $T_{12}$ being returned to the non-conductive state whereupon the input to amplifier 68 will return to the level $U_E$ commensurate with the number stored in memory 74. Accordingly, the original constant current I is reestablished by operational amplifier 68 at a level determined by the information in storage device 74 as processed by analog to digital converter 42. The effect of the incorporation of amplifier $T_{11}$, flip-flop 84, monostable multivibrator 86 and gating transistor $T_{12}$ is thus to cause an interruption of the constant current I following termination of the gate signal 48 until such time as the voltage on sweep voltage generator 24 output bus 28 is equal to the desired sweep voltage base level as defined by Zener diode $ZD_1$.

The above-described circuitry is particularly well suited for oscilloscope type display devices which are provided with a microprocessor for performing functions such as, for example, the processing of measured signals.

The above-described apparatus may be used with particular advantage in multi-trace oscilloscopes in which each channel requires a different sawtooth waveform rise time; i.e., each channel has its own X-deflection rate. In such an environment, the microprocessor may automatically calculate the required coarse and fine values for the traversing times and store these values. When the X-deflection plates are switched to a new channel, the microprocessor automatically places these new values for the traversing time in the storage devices 70 and 74. New calibrations of the different $t_H$ times are not required.

The apparatus of FIGS. 1–3 is particularly well suited for use in ultrasonic test equipment wherein the keyboard 44 may be used to enter data regarding the desired display width, for example 0–200 mm, as well as the kind of material to be tested and data related to the type of test element or head. The data related to the test apparatus will be a delay commensurate with the distance the ultrasonic signal must travel between the transducer and work. In other words, in the ultrasonic test apparatus environment, the slope of the sawtooth waveform is not entered in terms of the time of traversal of the electron beam across the display but rather as the distance of travel of the ultrasonic beam in the test object. This travel distance may, for example, be 0 to 200 mm. The propagation of the beam of ultrasonic energy is a function of the velocity of propagation of sound in the test object. This propagation velocity, in turn, relates the depth of penetration of the pulse of ultrasonic energy in the test object to the elapsed time until an echo may be expected from the selected examination depth. Data to be entered via keyboard 44 is thus the desired depth of inspection within the test object and the applicable velocity of propagation of ultrasonic energy. From these relations, it is possible to derive an appropriate electron beam traversing time which will be commensurate with the passage of the ultrasonic test signal through the desired test area. However, as noted above, consideration must be given to the fact that the ultrasonic signal must first cover a distance between the piezoelectric transducer element in which it is generated and the beginning of the test region within the test object. This distance is also entered into the apparatus via the keyboard 44. To be more explicit, the delay or pretravel distance is actually comprised of the distance between the transducer and the surface of the test object, presuming that the ultrasonic probe head is in contact with the test object, and a second distance defined by the path length of the ultrasound energy in the test object to the beginning of the region to be examined. The initiation of the deflection of the electron beam in the cathode ray tube must be delayed by a given amount of time, hereinafter referred to as the trigger delay time, which is a function of the time required for the ultrasonic beam to traverse the above-explained delay distance. This time delay is produced by a trigger delay circuit which will be described below.

Figure 5:
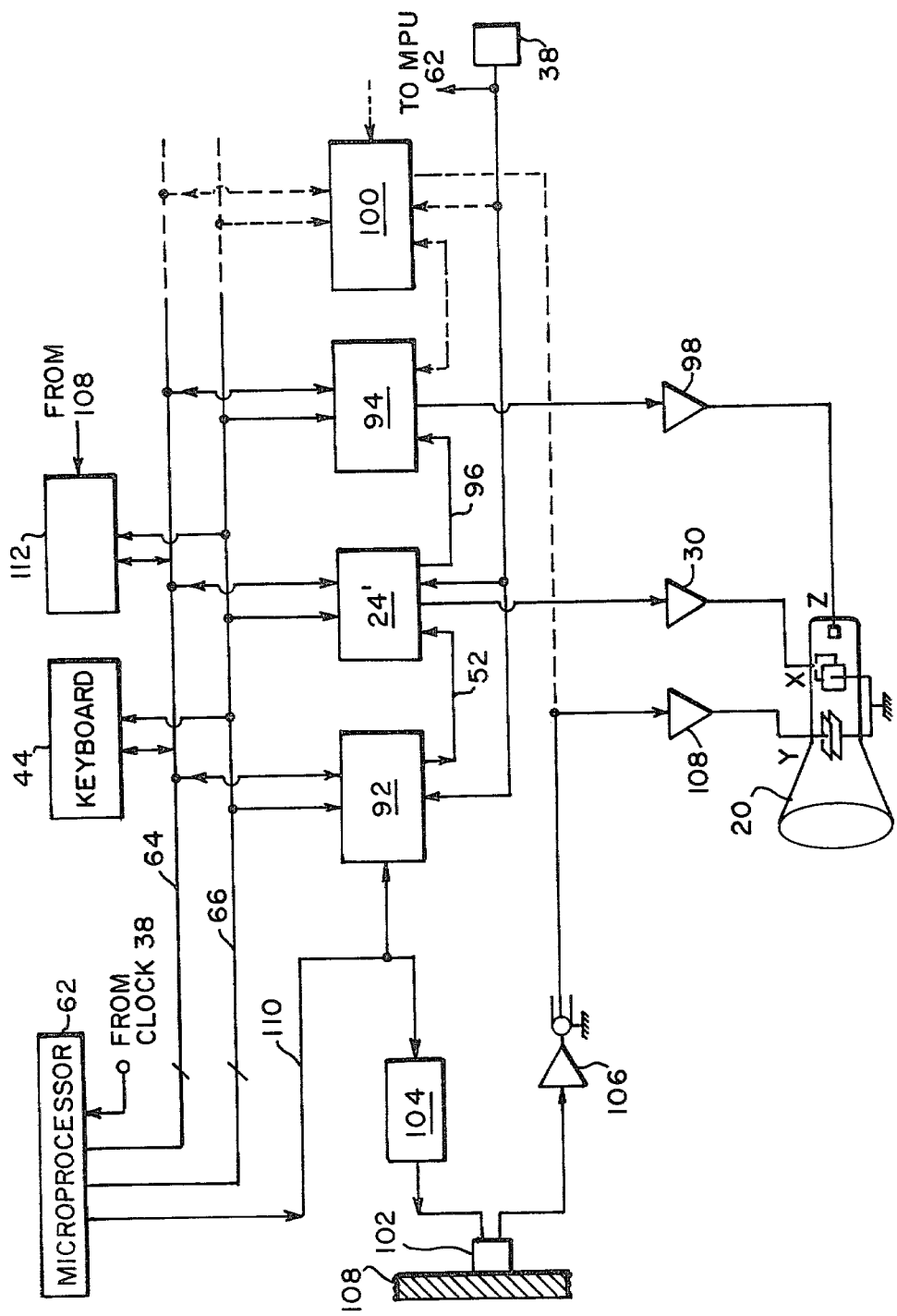
FIG. 5 is a functional block diagram of ultrasonic test apparatus employing the circuitry depicted in FIGS. 1-3.

With reference now to FIG. 5, a portable ultrasonic test instrument in accordance with the present invention is shown by means of a functional block diagram. As described above, the microprocessor 62 is connected to the multi-conductor data and address buses which are indicated at 64 and 66 respectively. The keyboard 44 is also connected to the data and address buses and, via the buses, will supply the input parameters commensurate with the test conditions to microprocessor 62. A sweep voltage generator 24' is also connected to the data and address buses 64 and 66 and provides, in the manner described above in the discussion of FIGS. 2 and 3, a sawtooth voltage waveform to the input of deflection voltage drive amplifier 30. The output of amplifier 30 is impressed across the X or horizontal deflection plates of cathode ray tube 20. The sweep voltage generator 24' includes the above-described sawtooth voltage generator 24, storage devices 70 and 74, decoder 76, analog to digital converter 42, Schmidt trigger 32 and counter 36. A trigger delay circuit 92 is also connected to the data and address buses and, like the sweep voltage generator 24', receives an input from the clock pulse source 38. The output of trigger delay circuit 92 comprises the set pulses for flip-flop 32 in sweep voltage generator 24'. These pulses are delivered to the sweep voltage 24' via conductor 52 (see also FIGS. 1 and 2) to initiate each cycle of the sawtooth voltage waveform.

In the customary manner, the electron beam in cathode ray tube 20 is to be gated on, thus generating a visible display, only during the traversal time $t_H$. The "blanking" of the screen of CRT 20 during the fly-back portion of the cycle of the output voltage of the sweep voltage generator 24' is accomplished under the command of a control unit 94. The control unit 94 receives a "beam release" signal from the sweep voltage generator 24' via conductor 96. The gating signal provided by control unit 94 is applied to CRT 20 by amplifier 98. Control unit 94 is also connected to the data and address buses 94 and 96.

Additional circuit elements, generally indicated at 100 in FIG. 5, may also be connected to microprocessor 62 via the data and address buses. These additional elements will be discussed below.

The drive or energizing signal for a transducer 102, which generates the beam of ultrasonic energy, is produced by an excitation or drive circuit 104 upon the receipt thereof of a pulse from microprocessor 62. Any returning echo signals are detected by transducer 102 and converted into electrical signals which are applied to amplifier 106. The amplified echo signals which appear at the output of amplifier 106 are delivered to the Y or vertical deflection plates of CRT 20 via a further amplifier 108. To give an example of operation of the apparatus of FIG. 5, if it is desired to test for defects in a steel workpiece 108 at a depth of between 20 and 50 mm, these depths values are entered into the apparatus by means of keyboard 44. The velocity of sound in steel and the delay distance mandated by the physical characteristics of the transducer head are also entered via keyboard 44. The microprocessor 62 then calculates the trigger delay time; i.e., the time during which the switch $S_9$ of the sawtooth generator (see FIGS. 2 and 3)

is to remain closed. This time corresponds to the delay distance of the ultrasonic beam until it reaches a depth of 20 mm in the test object. When this distance has been traversed, the sawtooth waveform for X-deflection of the electron beam in CRT 20 will begin. The required traversing time $t_H$ of the sawtooth waveform is also calculated by microprocessor 62. The calculated times are expressed in the form of quantities of clock pulses on the basis of a clock frequency $f_o$ which is dependent upon the required resolution or display accuracy. For example, if a resolution of 0.3 mm is required to detect faults in workpiece 108; i.e., if faults of this magnitude must be reliably detected; then the clock frequency needed with ultrasonic signals whose longitudinal velocity of propagation is $c_{steel}$ (applicable for normal probes) is given by:

$$f_o = c_{steel}/2(0.3) = 10 \text{ MHz (approximately)}$$

The overall trigger delay time $t_{KV}$ is the sum of the pretravel (delay) time $t_{SV}$ in the probe head (transducer 102) and the delay time $t_M$ within the test object which, in the present example, corresponds to a penetration depth of 20 mm. The delay time $t_{SV}$ in the probe may be calculated from the probe delay distance $S_V$ divided by the propagation speed of ultrasonic energy in the probe, $c_V$, while the delay time $t_M$ in the test object may be calculated by dividing the path $S_M$ within the test object by the ultrasonic propagation velocity $c_M$ in the test object. The quantity of pulses corresponding to the correct trigger delay time is given by:

$$N_{KV} = 2f_o[(S_V/C_V) + (S_M/C_M)]$$

The quantity of pulses corresponding to the display width; i.e., the traversing time of the sawtooth waveform; is given by:

$$N_{BB} = 2f_o(S_{BB}/C_M)$$

where $S_{BB}$ is the depth range in the test object which, in the example being described is 30 mm.

The pulse count $N_{KV}$ is delivered from microprocessor 62 to trigger delay circuit 92 via data bus 64 while the pulse count $N_{BB}$ is delivered to the sweep voltage generator 25 via the data bus. Subsequently, microprocessor 62 generates a trigger pulse which, via conductor 110, is supplied to the excitation circuit 104 and to the trigger delay circuit 92. Accordingly, the transducer 102 will be excited and will produce a burst of ultrasonic energy. At the same time, the trigger delay circuit 92 is released and starts to count down the pulse count $N_{KV}$ which defines the trigger delay time $t_{KV}$. After the expiration of the trigger delay time, a trigger pulse will be delivered from delay circuit 92 to the sweep voltage 24' where, in the manner described above, it will cause the setting of flip-flop 34 and the opening of switch $S_9$ thereby initiating the generation of the sawtooth voltage. Simultaneously with the onset of the sawtooth voltage, the electron beam current is enabled by amplifier 98 as a result of an output signal received from control unit 94 upon its receiving a command signal from sweep voltage generator 24' via conductor 96. Any signal commensurate with an echo received during the traversing time $t_H$ of the electron beam results in a vertical (Y) deflection of the electron beam and constitutes a fault indication in the test object. The apparatus depicted in FIG. 5 includes a data recording device 112 which may, for example, be a cassette-type recorder connected to both the data and address buses for recording the ultrasonic test results.

Figure 6A:
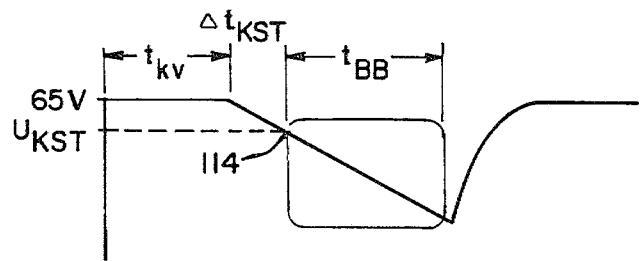
FIGS. 6a and 6b are sweep voltage waveform diagrams which facilitate understanding of further novel features of the present invention.
Figure 6B:
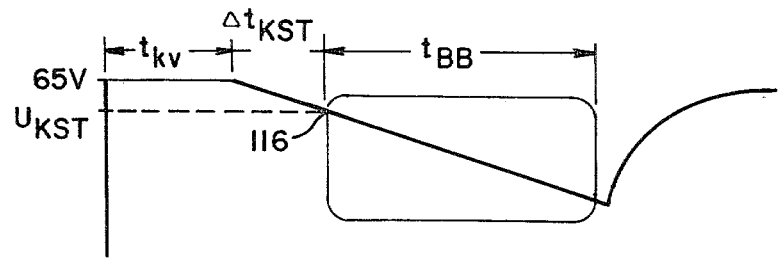

FIGS. 6a and 6b illustrates how the pulse count number $N_{KB}$, computed according to formula (2) above, may be corrected pursuant to a further novel feature so as to obtain the best possible visual display on the cathode ray tube. These improved results are based upon the following considerations. Firstly, the normal storing point for the electron beam of an oscilloscopic display is a point, indicated in FIG. 6a as 114, which is usually at the left margin of the display. The electron beam will be directed to this point when the horizontal deflection voltage magnitude is $U_{KST}$ and has a value which is usually smaller than the base line voltage $U_Z$ of the sawtooth waveform; the base line voltage being 65 volts in the example being described. After expiration of the trigger delay time $t_{KV}$, which is defined by the pulse count number $N_{KV}$, the sweep voltage generator is released and the linear portion of its sawtooth waveform output voltage is initiated. The time $t_{KST}$ which elapses until the electron beam has been deflected to point 114 depends on the slope of the sawtooth waveform. As shown in FIG. 6b, if the slope is shallow the actual image starting point 116 is reached at a later time than would be the case with a steep slope. Accordingly, it is appropriate to delay the onset of the sawtooth voltage as a function of the slope of this signal. The delay of the trigger starting point can be derived approximately from the formula;

$$\Delta t_{KST} \approx a \cdot t_{BB}$$

where $a$ is a constant which depends on the desired image starting point and $t_{BB}$ is equal to the traversing time $t_H$ of the electron beam and corresponds to the time during which it is possible to observe the beam on the screen in its motion from left to right. The resulting corrected pulse count number thus is:

$$N'_{KV} = N_{KV} - aN_{BB}$$

Figure 7:
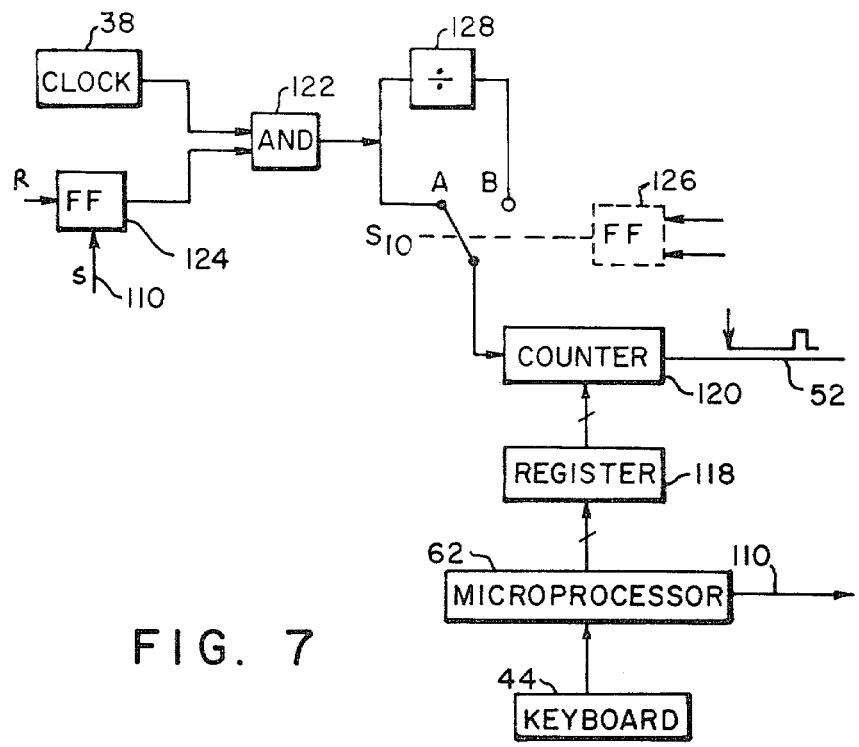
FIG. 7 is a circuit block diagram of a trigger delay circuit in accordance with the present invention and suitable for use in the apparatus of FIGS. 2 and 5 to produce the waveforms of FIGS. 6a and 6b.

FIG. 7 is a block diagram of a circuit which may be employed as the trigger delay circuit 92 of FIG. 5. The pulse count number $N_{KV}$, calculated by microprocessor 62 on the basis of data entered via keyboard 44, is loaded into a register 118 and then supplied to a binary counter 120. The counter 120 also receives input pulses from a source which includes AND gate 122 and switch $S_{10}$. The inputs of AND gate 122 are respectively connected to the output of clock pulse generator 38 and an output of flip-flop circuit 124. A further flip-flop circuit 126 controls the state of switch $S_{10}$, which in actual practice will be a solid state device, so as to either directly connect the output of AND gate 122 to the input of counter 120 or to connect the output of a frequency divider 128 to the counter input. Thus, with switch $S_{10}$ in "position" A, the binary counter 120 sees an input pulse train at frequency $f_o$ whereas the counter receives a pulse train of frequency $f_o/10$ when switch $S_{10}$ is in "position" B. The ability to vary the input frequency to counter 120 makes possible a change in the effective image resolution as discussed above. If the trigger pulse generated by microprocessor 62 id delivered to flip-flop 124, the flip-flop will be set and AND gate 122 enabled. Since the appearance of a microprocessor generated pulse on conductor 110 corresponds to the ultrasound transducer being energized, the enabling of AND gate 122 will result in clock pulses being delivered to counter 120 starting from the time of generation of the beam of ultrasonic energy. The trigger delay number $N_{KV}$, which has been stored in register 118 and applied to counter 120, is counted down at either the frequency $f_o$ or frequency $f_o/10$ depending on the state of switch $S_{10}$. At the conclusion of the count, counter 120 will provide an output pulse on conductor 52 which commands the sweep generator 24' (FIG. 5) to initiate application of the sawtooth voltage to the deflection plates of CRT 20. That is, the pulse provided at the output of counter 120 comprises the signal which sets flip-flop 34 (FIG. 2) thus initiating the gating signal 48 which causes release of the sawtooth waveform.

A substantial advantage of the present invention resides in the fact that it permits the calibration of the imaging area of the CRT in terms of units of length. This calibration is based upon the provision of suitable traversing times of the electron beam; i.e., rise or fall times of the leading ramp of the sawtooth waveform which serves as the horizontal deflection or time base voltage. Direct calibrations of this nature have not previously been possible because of a lack of long-term stability of circuit components which resulted in the selected and actual values of the time $t_H$ varying in an unpredictable fashion. In the prior art, in order to compensate for such factors as component aging, it has been customary to recalibrate a CRT display by periodically conducting tests on test objects of known dimension. This type of recalibration is relatively time-consuming. In accordance with the present invention, such recalibration is unnecessary since any imaging region may be preselected by means of a keyboard entry and, once selected, will be maintained exactly by the continuous comparison of the nominal or set value and the actual value of the effective beam traversing time.

As previously described, the present invention permits the display of the results of the passage of the ultrasonic energy through a preselected range within the test object. This desirable result is obtained by causing the triggering of the sawtooth waveform, and thus the start of the CRT image field, after a given holding or trigger delay time has expired. The present invention also permits the selection of the length of the imaging region on the basis of the sawtooth voltage rise/fall time; i.e., the beam traversing time.

It may be desirable to provide for an automatic indication of the occurrence of echo signals resulting from the beam of ultrasonic energy intercepting faults within a given depth range within a test object. Such an automatic fault indication is also possible according to a further feature of the invention which will be described below. This feature, which will be referred to hereinafter as a "time and amplitude gate", defines and displays a "gate" bar on the CRT screen. Any echo related signal having an amplitude sufficiently large to deflect the electron beam to a vertical position which is greater than this "gate", and which occurs within the horizontal limits of this "gate", is automatically recognized and may serve to initiate an alarm or other action. The vertical and horizontal positions of the "gate" and its width should, advantageously, be selectable. Also, the "gate" is most desirably displayed on the CRT, for example in the form of a horizontal bar, between successive displays of actual data signals.

Figure 8:
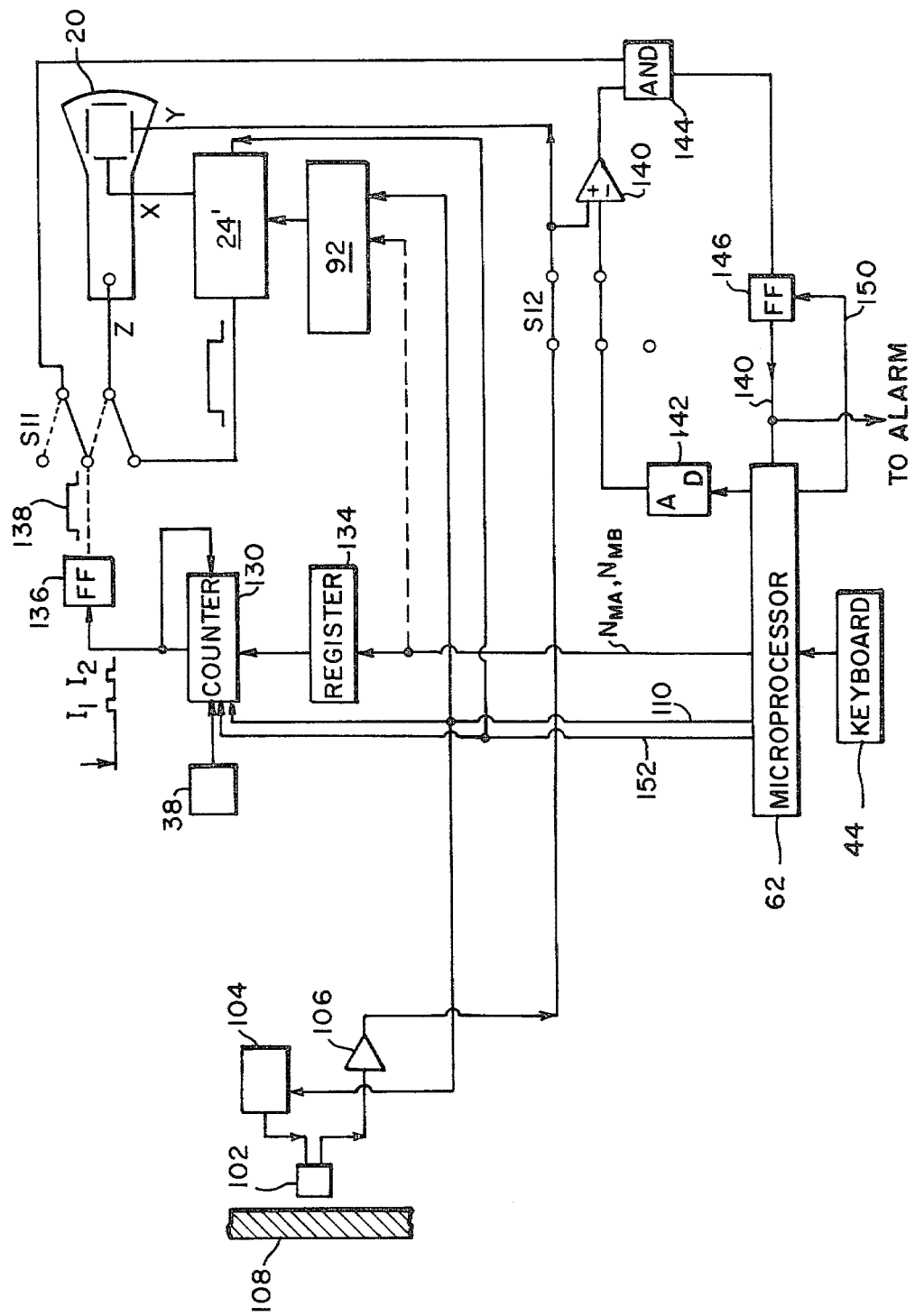
FIG. 8 is a functional block diagram of ultrasonic test apparatus in accordance with the present invention and employing time and amplitude gating control circuitry for the display.

Referring to FIG. 8, an ultrasonic test device is depicted which includes, as in the case of the apparatus of FIG. 5, a drive signal generator 104 which produces the excitation for the transducer 22 which generates the ultrasonic energy to be delivered into the test object or workpiece 108. It should be understood that the drive signal generator 104 may produce, in response to a gating pulse, a plurality of phase related output signals which have preselected waveforms. The test apparatus further includes an amplifier 106 which amplifies the echo-related signals produced by transducer 102. These echo signals are, under normal test conditions, applied to the Y deflection plates of CRT 20 to cause the vertical deflection of the electron beam in the known manner. The horizontal timing signal; i.e., a sawtooth voltage; is produced in the manner described above by sweep voltage generator 24'. The slope of the sawtooth voltage will be commensurate with the examination range of interest within the test object 108. The necessary holding time; i.e., the time which must elapse between the energization of transducer 102 and the start of the generation of the horizontal sweep voltage by generator 24'; is controlled by the trigger delay circuit 92 in the manner described above. The microprocessor 62 provides, on conductor 110, the start or trigger pulse signal for the transducer excitation signal generator 104 and a "start" signal for trigger delay circuit 92. The trigger pulse generated by microprocessor 62 is also applied as an input to counter 130 for the purposes to be described below. In FIG. 8 the data and address buses which interconnect the various subsystems have been omitted in the interest of facilitating understanding of the hardware. It is also to be noted that, in the apparatus depicted in FIG. 8, the gating of the electron beam in CRT 20; i.e., the function of the control unit 94 of the FIG. 5. apparatus; is controlled by an output of sweep voltage generator 24'. The CRT blanking control signal is indicated at 132 and is applied to CRT 20 via a first contact of a switch $S_{11}$.

The horizontal distance $S_A$ defining the start of the above-mentioned "gate" and its width $S_B$ are provided in the form of output signals from microprocessor 62. These numbers, $N_{MA}$ and $N_{MB}$, are serially loaded into a register 134. This numerical information is presented by register 134 to above-mentioned counter 130. The output of counter 130 is connected as an input to a flip-flop 136.

To understand the operation of the FIG. 8 apparatus, it may first be assumed that a number of data items are known and are available as digital values within the assigned memories of microprocessor 62. These data items include the characteristics of the test head or probe which includes transducer 102, the delay distance $S_V$ of the ultrasonic signal in the probe, velocity of sound $C_V$ in the probe and the velocity of sound $C_M$ in the test object 108. The operator will then select the desired "gate" constants; i.e., the starting position $S_A$, the width $S_B$ and the vertical position (amplitude) of the "gate". These parameters will be entered in terms of milimeters or percent of CRT display height by means of keyboard 44. The microprocessor 62 will then compute the corresponding internal data items on the basis of a stored program. These internal data items are the above-mentioned pulse count numbers $N_{MA}$, which defines the onset position of the "gate", and $N_{MB}$ which defines the width of the "gate". The clock frequency $f_o$ depends on the desired resolution; i.e., on the precision required in the image. As already discussed in connection with the overall image width, an image resolution of 0.3 mm in a test object made of steel in which the speed of propagation of longitudinal ultrasonic waves is $c_{steel}$ requires a clock frequency given by:

$$f_o = c_{steel}/2(0.3 \text{ mm}) = 10 \text{ MHz (approximately)}.$$

If $t_A$ is the time up to the occurrence of the "gate", i.e., the time which is the sum of the delay times in the probe and the test object; then the pulse count number defining the horizontal position of the "gate" is given by:

$$N_{MA} = 2f_o(S_V/C_V + S_A/C_M)$$

Where
$S_V$ is the delay distance in the probe;
$C_V$ is the velocity of sound in the probe;
$S_A$ is the delay distance in the test object; and
$C_A$ is the velocity of sound in the test object.
The pulse count number defining the "gate" width is given by $$N_{MV} = 2f_o(S_B/C_M)$$

where $S_B$ is the width of the "gate" in units of length. The calculated pulse number $N_{MA}$ is loaded into register 134 and, as noted, passed into counter 130. Subsequently, the pulse number $N_{MB}$ is loaded into register 134 wherein it remains ready to be passed to counter 130. Upon application of a trigger pulse from microprocessor 62 to conductor 110, counter 130 will be "opened" and will count down pulses provided by clock 38 at the frequency $f_o$. When the number $N_{MA}$ has been completely counted down, counter 130 will provide a first output pulse $I_1$ which sets the flip-flop 136.

The pulse $I_1$ is also fed back to the "load" input control of counter 130 thereby enabling the counter to receive the number $N_{MB}$ which is immediately counted down. When the number $N_{MB}$ has been totally counted down, counter 130 will provide a second output pulse $I_2$ which resets flip-flop 136. Accordingly, the flip-flop 136 will provide an output pulse which is indicated at 138. The signal commensurate with echoes received from the test object 108 and the "gate" are displayed alternately on CRT 20 under the control of switches $S_{11}$ and $S_{12}$. With these switches in the state shown in FIG. 8, the echo-related signals are delivered to the Y deflection plates of CRT 20 and displayed. These echo-related signals are simultaneously applied to the first input of a comparator circuit 140. The second input to comparator 140 is an analog signal produced by an analog to digital converter 142. Converter 142 produces an analog voltage which corresponds to the microprocessor generated digital value of the selected "gate" height. The output of comparator 140 comprises a first input to AND gate 144. The second input to gate 144 is the signal 138 generated by flip-flop 136; this second gate input being passed to AND gate 144 via switch $S_{11}$. If the output of comparator 140 indicates that the amplitude of the echo-related signal provided at the output of amplifier 106 is greater than the height (threshold) of the "gate" as represented by the output of converter 142, a pulse will be delivered to the first input of gate 144. If gate 144 is enabled by the output of flip-flop 136 when the echo signal is larger than the "gate" height and falls within the width of the "gate", AND gate 144 will provide an output signal which causes the setting of a flip-flop 146. Flip-flop 144, when set, will provide an output signal on conductor 148 which may be delivered to an alarm. This signal commensurate with the setting of flip-flop 146 is also delivered to microprocessor 62 whereby the apparatus may be employed as a peak detector circuit. In such case the microprocessor will follow a program of gradually increasing the "gate" threshold until the output of AND gate 144 no longer indicates the existence of an echo signal. In other words, the microprocessor 62 may be employed to automatically increase the "gate" threshold value supplied to analog to digital converter 142 in step-wise fashion while the comparator 140 performs successive comparisons so that the maximum value of the echo signal may be determined. If such successive comparisons are to be performed, the microprocessor will provide, on conductor 150, reset signals for flip-flop 146.

If switches $S_{11}$ and $S_{12}$ are in the position shown by means of broken lines in FIG. 8, the CRT 20 will display the "gate". In order to display the "gate" microprocessor 62 will provide a command signal to counter 130 via conductor 152. This command signal will also be delivered as an input to the sweep voltage generator 24'. The signal commensurate with "gate" threshold which appears at the output of digital to analog converter 142 is applied via switch $S_{12}$ to the Y deflection plates of CRT 20 thereby causing the generation of a "bar" at the correct height on the screen. The output pulse 138 provided by flip-flop 136, which defines the horizontal position of the "gate" is delivered by switch $S_{11}$ as the blanking control signal to CRT 20. Accordingly, a horizontal bar representing the time and amplitude "gate" will be displayed.

Figure 9:
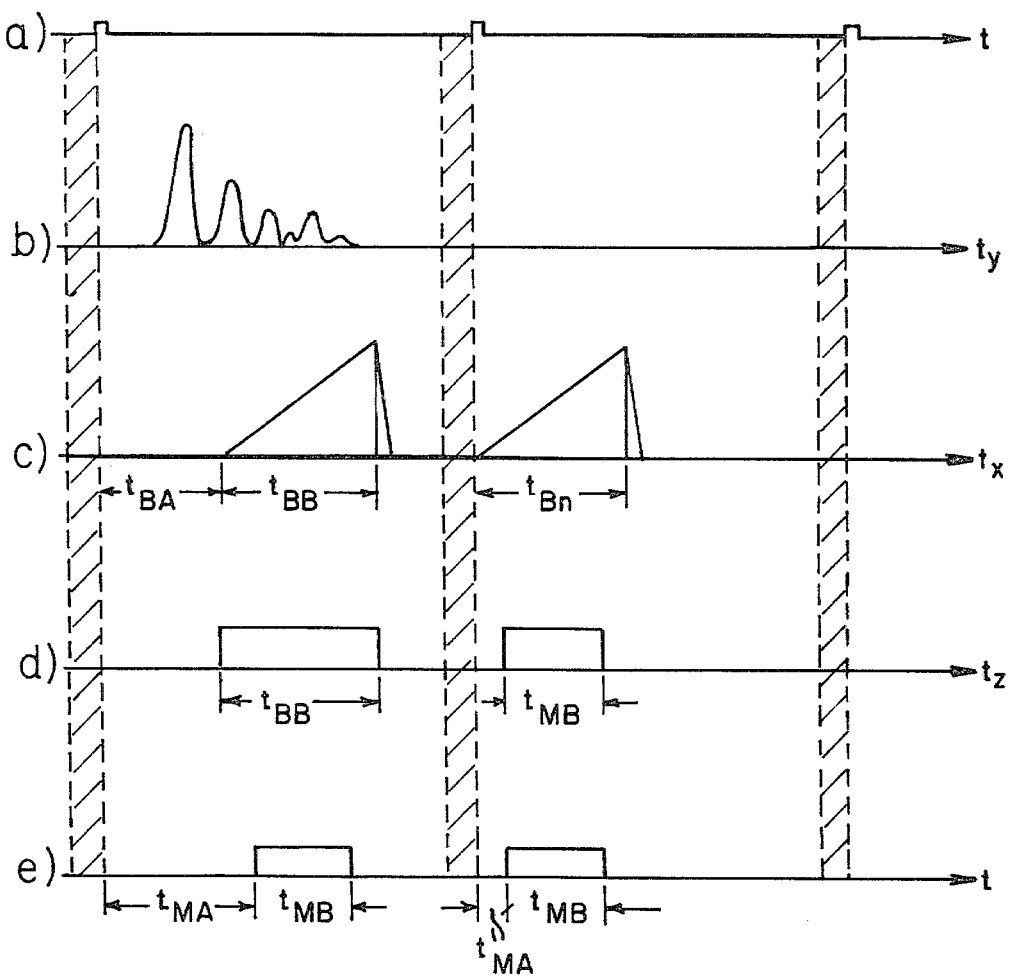
FIG. 9 is a timing diagram which facilitates understanding of the time and amplitude gating circuitry of FIG. 8.

FIG. 9 is a timing diagram which illustrates the timing of the various signals and events and will help to understand the operation of the above-described apparatus. In FIG. 9a, three successive trigger pulses as produced by microprocessor 62 on output conductor 110 are shown. The display of echoes received from the test object will occur between the first and second trigger pulses. If necessary, the microprocessor calculates the new pulse count number for the "gate" start, $N_{MA}$, and the number for the "gate" width, $N_{MB}$. These numbers are loaded into register 134 followed by the monitoring and indicating of the occurrence of an echo signal within the defined "gate" with an amplitude exceeding the vertical position of the "gate". After the switches $S_{11}$ and $S_{12}$ have switched from the position shown in solid lines in FIG. 8 to the position shown by broken lines, the "gate" bar is displayed between the second and third trigger pulses. This alternate operative mode may be repetitive. It has been found desirable to permit an intervening display of an echo signal, between alternate "gate" bars in the case where the "gate" is to be repetitively displayed, in order to maintain adequate brightness of the echo signal. Due to the fact that the individual sequential displays follow one another with great rapidity, an observer will perceive all events simultaneously.

FIG. 9b depicts the signal applied to the vertical (Y) deflection plates of CRT 20. Between the first and second microprocessor generated trigger pulses a typical echo-related signal is shown. The signal represented as being applied to the vertical deflection plates between the second and third trigger pulses is a voltage corresponding to the "gate" height. This voltage would typically not be displayed as a continuous horizontal bar extending across the entire display. FIG. 9c shows the horizontal deflection voltage and it will be seen that, after the first trigger pulse, a holding time $T_{BA}$ is permitted to elapse by the action of the trigger delay circuit 92 before the sweep voltage generator 24' is energized so as to cause generation of the sawtooth waveform during the time $T_{BB}$. The enabling voltage which is applied to the CRT, to thereby permit the creation of a visible display, is generated only during the time $T_{BB}$ and the waveform of the echo signal is visible only during that time. The signal $t_{BB}$ is depicted in FIG. 9d between the first and second microprocessor generated trigger pulses. FIG. 9e illustrates the output signal 138 of flip-flop 136 and it will be noted that the flip-flop is set after a time $t_{MA}$ which is greater than the time $T_{BA}$, and that flip-flop 136 will be reset after a period $t_{MB}$ which is equal to the width of the "gate". The signal represented in FIG. 9e is applied as the enabling signal to AND gate 144 and will cause the setting of flip-flop 146 if the comparator 140 senses that the "gate" threshold has been exceeded. As described above, the setting of flip-flop 146 will result in the generation of an alarm signal. While the "gate" bar is being displayed; i.e., during the time period between the second and third microprocessor generated trigger pulses; the vertical (Y) deflection plates of CRT 20 have applied thereto the signal supplied by analog to digital converter 142 as shown in FIG. 9b. The horizontal (X) deflection plates receive the sawtooth voltage provided by sweep voltage generator 24' which has the same traversing or rise time $t_{BN}$ as the traversing time $t_{BB}$ utilized during the echo imaging cycle. These relations are shown in FIG. 9c. During the time $t_{MB}$ represented in FIG. 9d, the screen displays the "gate" bar because of the presence of a control signal from flip-flop 136 as indicated between the second and third trigger pulses in FIG. 9e. The time $t'_{MA}$ represented in FIG. 9e indicates the time span between the onset of the sawtooth voltage and the initiation of the signal for representing the "gate" bar; i.e., the onset of the "gate" bar display. Accordingly, the pulse count number for the start of the bar display is:

$$N'_{MA} = N_{MA} - N_{BA}$$

The advantage of advancing the "gate" bar start by the time $t_{BA}$ resides in the fact that more time is available for further processing and the next trigger pulse can be produced at an earlier point in time.

The alternate trigger pulses applied to conductor 110; i.e., the trigger pulses employed to initiate the display of the "gate" bar; do not have to be applied to the transducer driver 104 since echo signals received during the time that the "gate" bar is displayed will not be processed.

Figure 10:
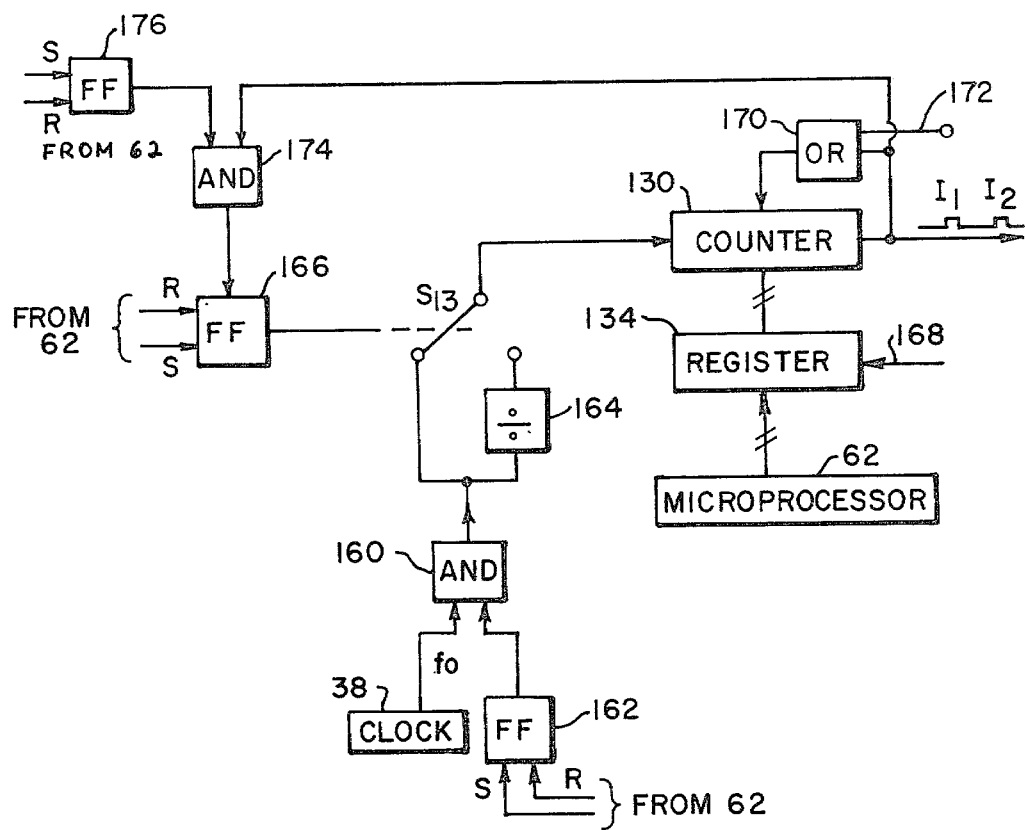
FIG. 10 is a circuit block diagram which depicts additional details of the gating control circuitry of FIG. 8.

FIG. 10 depicts, in block diagram form, a preferred circuit for generating the pulses $I_1$ and $I_2$ which respectively cause the setting the resetting of flip-flop 136 of FIG. 8. As explained above, these pulses are commensurate with the timing, or more precisely the width, of the time and amplitude "gate". The microprocessor 62, as described above, delivers the digital signals commensurate with the numbers $N_{MA}$ and $N_{MB}$ to register 134. These digital values are serially loaded into counter 130 as described above. Register 134 may, for example, be a commercially available register of type SN 74C 374 while counter 130 may be a binary down-counting counter comprised, for example, of a pair of type SN 74 191 commercially available counters connected in series.

Continuing to discuss FIG. 10, a first input to an AND gate 160 comprises a series of pulses at frequency $f_o$ derived from the clock 38. The second input to gate 160 comprises the output of a flip-flop 162. Depending upon the position of a switch $S_{13}$, which performs the same function as the switch $S_{10}$ of FIG. 7, clock pulses passed by gate 160 are either directly delivered to counter 130 or are divided in frequency divider 164 before being applied to counter 130. The state of switch $S_{13}$ is controlled by a flip-flop circuit 166. Microprocessor 62 applies control signals to a register 134 via conductor 168 and to an OR gate 170 via conductor 172. OR gate 170 provides an output signal which controls the transfer of the counts from register 134 into counter 130. Microprocessor 62 also provides the set and reset input signals to the flip-flop 162 and the set and reset control signals to the flip-flop 166. A control signal on the control input 168 to register 134 causes the pulse count number $N_{MA}$ to be loaded into the register. Sequentially, the control signal at input 172 to OR gate 170 causes loading of the pulse count number $N_{MA}$ into counter 130. The pulse count number $N_{MB}$ is loaded into register 134, in response to a second control signal on input 168, subsequent to the transfer of the count $N_{MA}$ into counter 130. Accordingly, the number $N_{MB}$ is available for processing at the up-count inputs of counter 130.

Control signals from microprocessor 62, as noted above, determine the state of flip-flop 166 and thus control the setting of switch $S_{13}$ whereby the input pulses to counter 130 are either at frequency $f_o$ or frequency $f_o/10$.

The counting process is initiated by a trigger signal supplied by microprocessor 62 to the set input of flip-flop 162. The setting of flip-flop 162 enables gate 160 thereby initiating the delivery of pulses to counter 130. When the $N_{MA}$ pulse number has been counted down to 0, the $I_1$ output pulse from counter 130 will be generated and applied as an input to OR gate 170 and AND gate 174. This $I_1$ signal is also delivered, as discussed in the description of FIG. 8, as an input to flip-flop 136. The application of the $I_1$ pulse to OR gate 170 results in this gate producing a signal which clocks the $N_{MB}$ number from register 134 into counter 130. The clock pulses arriving at counter 130 via switch $S_{13}$ then count the $N_{MB}$ number down and, when the count reaches 0, and $I_2$ pulse is generated thus signifying termination of the time and amplitude "gate".

It is possible to perform the counting of the numbers commensurate with the onset and width of the time and amplitude "gate" with different frequencies. The foregoing will, for example, be necessary if one of the numbers exceeds the capacity of counter 130. For this purpose, flip-flop 166 is connected to receive an input signal from AND gate 174. The second or enabling input of gate 174 is provided by the output of a flip-flop circuit 176. The flip-flop circuit 176 is set and reset by pulses supplied by microprocessor 62. After the time before the onset of the "gate" has expired, the pulse $I_1$ may be employed to change the state of switch $S_{13}$ if the appropriate control signal is present at the set input of flip-flop 176 whereby gate 174 would be enabled and the $I_1$ pulse applied to flip-flop 166.

A significant advantage of the above-described circuit is that the dimensions of the time and amplitude "gate" can be entered directly via the keyboard 44 in units of length (mm or inches) and will cause the correct positioning of the bar which represents the "gate" on the screen of the CRT. All of the relevant data and parameters, such as the delay distances and the speed of sound in the probe and in the test object, are taken into account by the microprocessor during the calculation of the corresponding pulse numbers. Accordingly, in operation of the present invention it is unnecessary to set the parameters of the time and amplitude "gate" with analog devices, such as potentiometers, while making a manual final calibration.

Figure 11:
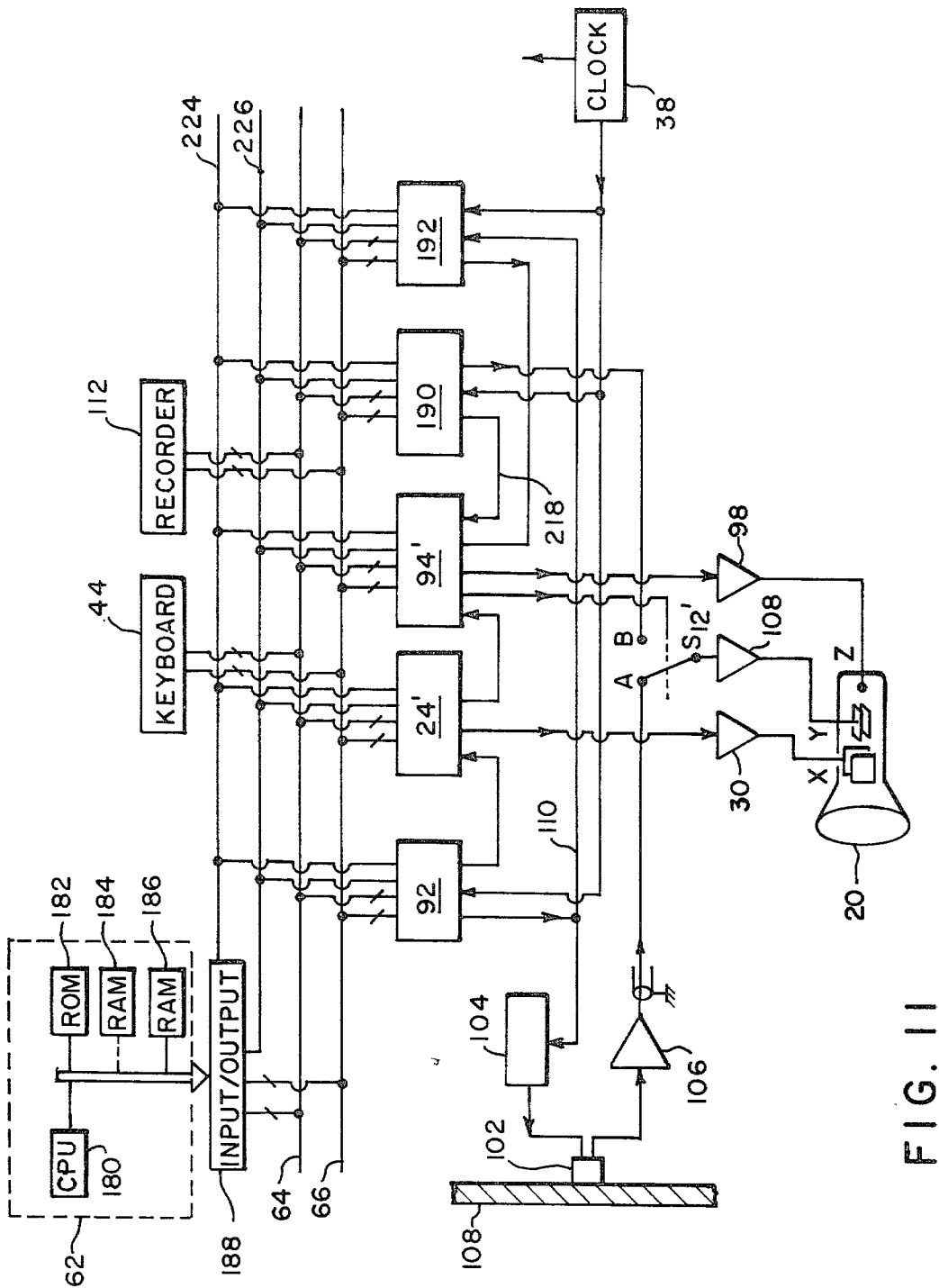
FIG. 11 is a functional block diagram, similar to FIG. 5, depicting ultrasonic test apparatus in accordance with the present invention in greater detail.

FIG. 11 is a functional block diagram of a further embodiment of an ultrasonic test instrument in accordance with the present invention. As depicted in FIG. 11, the microprocessor 62 includes a CPU 180, a read only memory 182 and a random access memory 184. The microprocessor further includes a random access read-out memory 186; all of these devices being connected to an internal bus in the manner known in the art. Microprocessor 62 is connected to eight line data and address (control) buses, respectively indicated at 64 and 66, via input/output circuit 188. The microprocessor 62 may, for example, be a Mostek type Z80. The microprocessor may be programmed using the "Assembler" language as explained in the "Microcomputer Systems Operations Manual" published by Mostek, Inc., publication number ASMB-80. The apparatus depicted in FIG. 11 includes the transducer drive signal generator 104, an ultrasound transducer 102 and an echo signal amplifier 106. The transducer drive signal generator 104 is activated by receipt of a trigger pulse delivered thereto via conductor 110 whereby a beam of ultrasonic energy will be transmitted into the test object 108. The ultrasonic beam transmission trigger pulse is generated by microprocessor 62 and, in the FIG. 11 embodiment, is delivered to the drive signal generator 104 via I/O circuit 188 and the trigger delay circuit 92. Thus, the trigger pulse applied to the transducer drive signal generator 104 will be produced after a time delay.

The pulse of ultrasonic energy transmitted into the test object 108 may encounter structural faults which cause echoes that are reflected back to transducer 102. These echoes are converted into electrical signals by the transducer and these echo signals are subsequently amplified in the receiver/amplifier 106. The amplified echo signal is, with a switch $S_{12}'$ in the "A" position shown by solid lines, delivered to a vertical drive amplifier 108 and, via the amplifier output, applied to the Y deflection plates of cathode ray tube 20. The horizontal (X) deflection plates of CRT 20 provide the time base for the display and are connected to the output of an amplifier 30 which is driven by sweep voltage generator 24. A control unit 94' provides the necessary beam; i.e., Z-control; signals to a Z-axis amplifier 98; this control signal being present during the time the sawtooth voltage is applied to the X deflection plates. Microprocessor 62 is connected to receive, via the data and address buses, the data entered via keyboard 44 and a recording device 112 is employed for storing test data. A screen writing circuit 190, which will be described in greater detail below, is also included in the system. Circuit 190 may cause the display of alpha numeric text on CRT 20 when the switch $S_{12}'$ is in the B state. The apparatus of FIG. 11 also includes a time and amplitude gate circuit, indicated generally at 192, which includes those above-described elements which generate the signals which cause the display of the "gate" bar. A clock pulse generator 38 delivers timing pulses to the trigger delay circuit 92 as well as to the screen writing circuit 190 and the time and amplitude gate control circuit 192. The state of switch $S_{12}'$ is controlled by an output of control unit 94'. All of the above-described subsystems are interconnected via the data and address buses as well as by direct connection as shown.

Figures 12, 13:
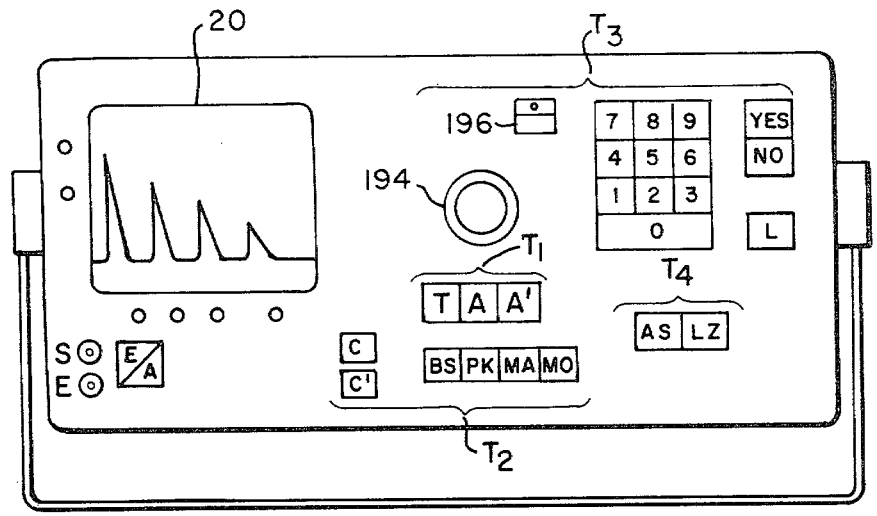
FIG. 12 is a front view of a control and display panel in accordance with one embodiment of the present invention.
FIG. 13 represents the presentation of alpha numeric information on the display depicted in FIG. 12.

Referring to FIG. 12, an ultrasonic test instrument in accordance with the present invention is shown in front elevation. The instrument of FIG. 12 will include all of the circuitry depicted in FIG. 11 with, of course, the exception of the transducer 102. The front panel of the instrument includes the face of the CRT 20 and four groups of data entry devices which have been indicated respectively at $T_1$ through $T_4$. Data entry group $T_3$ includes a rotary control knob 194 and a multiplier control push-button 196. Group $T_3$ also includes the standard numerical keyboard which has previously been indicated by reference numeral 44. The various data entry devices are of commercial origin and are available, for example, from Datanetics/Knitter. The key operated switches must, of course, be provided with suitable coding circuits, for example matrix-type coding circuits so that the operation of a given key produces an acceptable binary datum for the microprocessor.

The keyboard group $T_1$ includes the three keys T, A and A' which provide control inputs which define the basic mode of operation of the instrument. Depression of key T causes the instrument to function in the manner of a data terminal wherein printed text is placed on the screen of CRT 20 in the manner to be described below. Actuation of key A causes the well known A-representation which provides for the display of echo signals from faults in the test object. Actuation of key A' provides for display of the A-type representation with simultaneous display of at least a first line of text. The key group $T_2$ includes four keys related to basic functions. Thus, a key labeled BS is for screen data, a key PK is for probe data, a key MA is for material data and a key MO is for gate data. Actuation of any of these keys provides data entry access to the respective memory in microprocessor 62 where the input information to be supplied subsequent to the depression of the particular key is to be stored. The key group $T_2$ also includes keys C and C' which can be used to move a cursor vertically, using key C, or horizontally, using key C'. If the cursor is placed on a particular line or column in the display, he keys in group $T_3$ provide access to the memory location related to the cursor position.

The key group $T_4$ consists of two special function keys. The key labeled AS, when actuated, provides for storage of the A-image representation. The key labeled LZ permits measurement of the propagation time of the ultrasonic signal.

FIG. 13 exemplifies the text data which may be displayed on the screen of CRT 20 upon actuation of key T of key group $T_1$ and the actuation of key MO of key group $T_2$. The data displayed are those which had previously been entered into memory through manipulation of the keys of group $T_3$. The display includes a movable cursor, an unchanging explanatory text, variable data taken from memory and changeable by manipulation of the appropriate keys of group $T_3$ and suitable dimensions. Referring again to FIG. 11, if key MO is actuated, the text and dimensions are read out of the ROM 182 into the appropriate section of RAM 186. The changeable parts of the display are read from RAM 184 and placed in the corresponding sections of memory 186. By placing the cursor at the proper location with the aid of keys C and C', and actuating the keys in the group $T_3$, the stored data may be altered at will and is then displayed on the screen. The complete text is continuously displayed until a different set of keys is actuated.

When the entry of the operating data is complete; i.e., when the various parameters relating to the CRT, the probe (delay distance, sound velocity, etc.), the test object (sound velocity, etc.) and the time and amplitude "gate" (on set, width, threshold, alarm and peak detector) have been entered by use of the various keys in group $T_2$, the key A is depressed whereupon microprocessor 62 begins to compute from the entered data the required count numbers N for the trigger delay circuit 92, the sweep voltage generator 24' and the gate control circuit 192 in the manner described above.

Subsequently, the screen displays the A image corresponding to the test object 108; i.e., the echoes reflected from inhomogeneities within the workpiece which lie within the selected depth (examination) range. The adjustments required to account for the various characteristics of the probe, the material comprising the workpiece and the characteristics of the CRT are all automatically taken into consideration so that no further calibration is required. During this display the switch $S_{12}'$ of FIG. 11 is in the position shown in solid lines.

As explained above, when the holding time $t_{BA}$ computed by microprocessor 62 has expired (see FIG. 9c), the trigger delay circuit 92 produces a pulse which triggers the generation of the sawtooth voltage having a slope or traversal time $t_{BB}$ also as computed by the microprocessor. The sawtooth voltage is applied to the horizontal (X) deflection plates of cathode ray tube 20. The sawtooth voltage is also employed to generate the intensity or blanking control signal by causing the control unit 94' to produce a rectangular pulse for the duration of the sweep time of the electron beam in the CRT.

Figure 15:
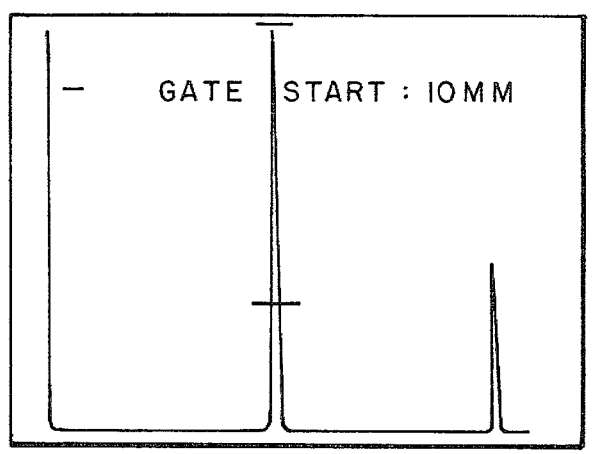
FIG. 15 is a representation of a display of the results of a test performed with test apparatus in accordance with the present invention.

If key A' is depressed rather than key A, indicating the desire to display echo-related signals and text simultaneously, the line of text appears on this screen in addition to the echo signals. The line of text which will be displayed is the line to which the cursor (see FIG. 13) has been caused to point. This display condition is depicted in FIG. 15. In the display mode represented by FIG. 15, the switch $S_{12}'$ of FIG. 11 is caused to alternate between its two possible states. In position "A", in which it resides for approximately eighteen ms, the screen depicts the echo signal one or more times. In position or state "B", in which the switch resides for approximately two ms, the line of text is displayed. Due to the relatively short dwell times and the rapid repetition rate, the user will perceive a composite display. It is to be noted that FIG. 15 also represents a display wherein the time and amplitude gate bar is visible in the position it occupies when a number of input commands have been generated by means of the control panel of FIG. 12. These input commands are commensurate with the actuation, in key group $T_2$ of key MO indicative of a desire to display the "gate" function. The cursor is then positioned to the line marked "display" and the key marked "YES" in key group $T_3$ turns on the "gate". When key A or A' of group $T_1$ is actuated, the gate bar is displayed on the screen. In the case of actuation of key A', the trace commensurate with the ultrasound echo will be displayed for eighteen ms and subsequently the "gate" bar and a line of text will be displayed for approximately two ms.

Figure 14:
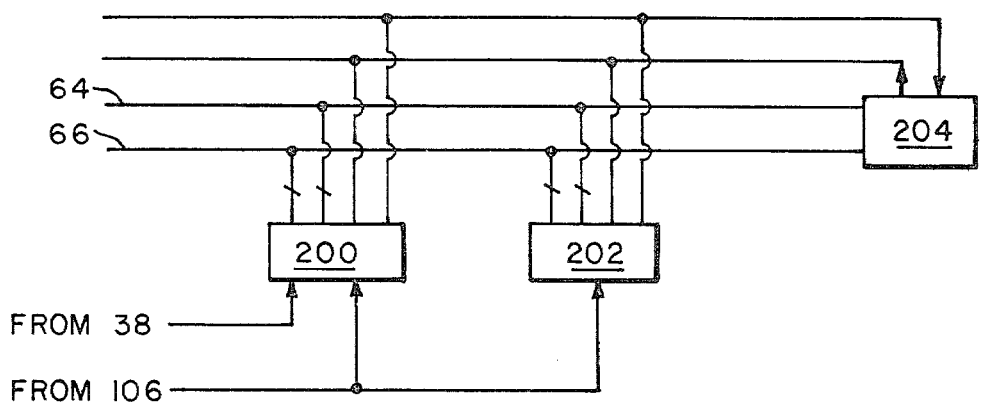
FIG. 14 is a functional block diagram showing additional details of the test apparatus of FIG. 11.

Referring now to FIG. 14, a block diagram of a portion of the circuitry represented by FIG. 11, with some additional elements, is shown. The additional elements which are added to the apparatus pursuant to the embodiment of FIG. 14 include a transit time meter 200, and "A-image" converter 202 and an interface unit 204 for connecting the instrument to an external processing device, not shown. Employing the circuitry of FIG. 14, the echo signal can be presented to the A-image converter 202 where it is converted into digital values which can either be stored in the RAM 184 of microprocessor 62 or in the recording device 112. This process is initiated by depression of key AS in key group $T_4$. The screen then shows the text line "RECORDING" and, when the key "YES" key group $T_3$ is pressed, the A-image is recorded in the memory. When the key LZ is pressed, the instrument measures the transit time of the ultrasonic signals in a known manner by means of the metering circuit 200 which receives the ultrasonic signal from amplifier 106 and a timing signal derived from clock 38.

Figure 16:
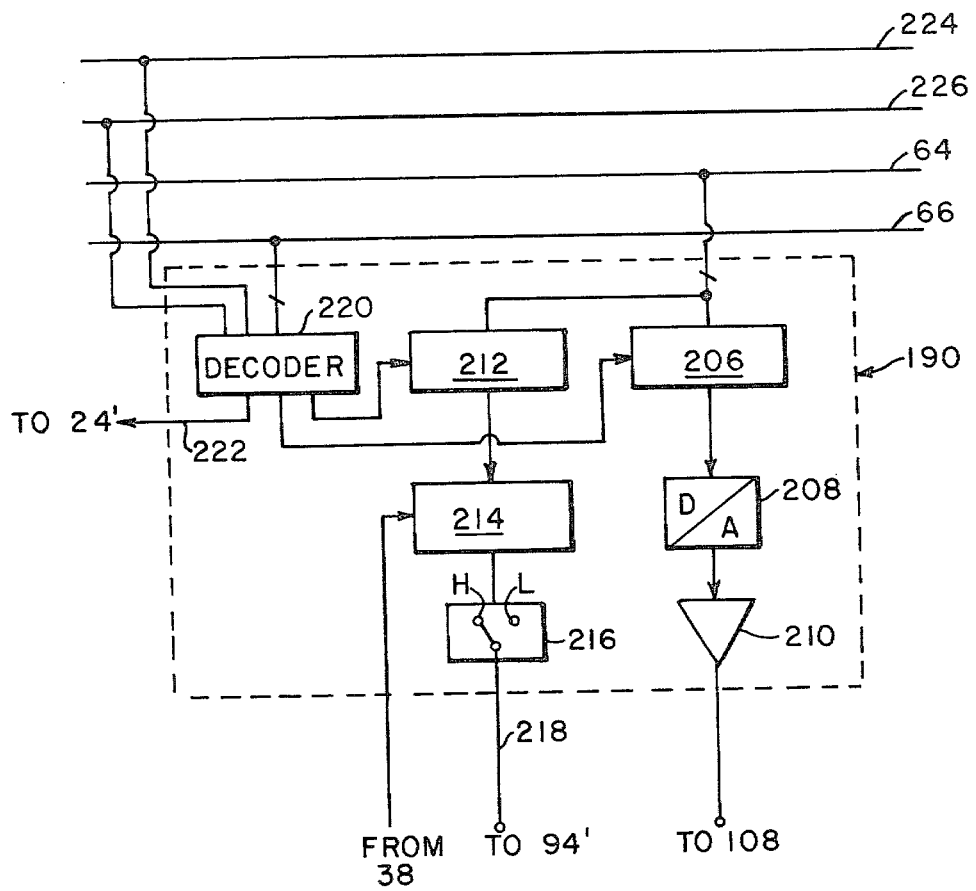
FIG. 16 is a functional block diagram of control circuitry for producing the alpha numeric display represented in FIG. 13.

The screen writing control 190 is shown in block diagram form in FIG. 16. This subsystem comprises basically two modules. The first module is responsible for the vertical (Y) deflection of the electron beam in the CRT and consists of an intermediate memory 206 which is connected to the data bus 64 of microprocessor 62. The first module also includes a digital to analog converter 208 and an amplifier 210 whose output is connected, via switch $S_{12}'$ when in the "B" state, to the Y deflection drive in amplifier 108. The second module of the screen writing control 190 consists of a second intermediate memory 212, also connected to data bus 64, a shift register 214 and an electronic switch 216. Signals appearing at the output of switch 216 are delivered as an input to the control unit 94' via conductor 218. The transfer commands for the two intermediate memories 206 and 212 pass from control or address bus 66 through a command decoder 220. A second input to shift register 214 is obtained from the clock 38. The decoder 220 may also pass a trigger pulse to sweep voltage generator 24' via conductor 222 to thereby cause the sweep voltage generator to initiate the generation of the sawtooth waveform. The decoder 220 is also connected, via conductors 224 and 226, to microprocessor 62.

The process of writing a line of text on the CRT will now be explained. If, for example, the key MA for material data is depressed, microprocessor 62 will transmit the appropriate material data to the readout RAM 186 and the digital information required to write the first line of text will pass over data bus 64 to the intermediate memory 206. This information serves to control the Y-deflection of the electron beam in the CRT. For this purpose, memory 206 is activated by a signal on address bus 66, delivered via the control decoder 220, if a "Ready" signal from the I/O circuit 188 is present at the input of decoder 336. A strobe signal is then returned, via conductor 226, to I/O circuit 188. Subsequently, the data stored in memory 206 will be provided to digital to analog converter 208 and the analog signal produced by the converter is amplified by amplifier 210 to produce a voltage $U_Y$ which, after further amplification in amplifier 108, is applied to the vertical (Y) deflection plates of the CRT. This will result in the electron beam, which at this time is prevented from impinging on the CRT screen, being aimed at the upper left corner of the screen.

Subsequently, the first brightness control byte is taken from RAM 186 and is loaded into memory 212 under the control of decoder 220. This digital value is transferred to register 214 which functions as a parallel to series converter. Register 214 thus causes the switch 216 to shift, at the clock frequency, between states commensurate with providing output signals of magnitude commensurate with a bright beam H and a dark beam L. The application of the clock signal to the input of shift register 214 is started only after the sweep voltage 24' has received the trigger pulse for starting the sawtooth voltage from decoder 220. Under the influence of the sawtooth waveform voltage, the electron beam in the CRT will travel from left to right along the upper image line and be modulated in intensity by the brightness control signals being taken out of shift register 334. This will, in the known manner, cause illumination of the image points on the CRT screen which constitute the line of text. While shift register 214 is emptied, the next intensity control byte required for the continuation of the text line is prepared for uninterrupted transfer to the shift register. After the passage of sixteen intensity control bytes, the electron beam will have arrived at the right edge of the screen; i.e., at the end of the first image line of the first line of characters. During the fly-back of the electron beam, no intensity control bytes reach output conductor 218 and thus no further points on the CRT screen are excited. Subsequently, the intermediate memory 206, the converter 208 and amplifier 210 reduce the vertical deflection voltage $U_Y$ by an amount equal to one image line of a line of characters so that the next sixteen intensity control bytes for forming the second image line of the first line of characters can be transmitted.

Each line of test characters is comprised of five image lines so that, after five complete writing processes, the first line of text is fully formed. At that time, the microprocessor will cause the electron beam to shift downwardly by a distance equal to three image lines and the generation of a second line of characters will be started. In a manner similar to that of a TV scan, the lines of text are composed by sequential horizontal scans. The total amount of textual information may consist of ten lines of text with twenty-one characters per line in the exemplary embodiment described herein. As already noted, each line of characters is composed of five lines of image points. After ten lines of text have been written, the electron beam will be aimed to the lower right-hand corner of the CRT screen.

The "gate" bar shown in FIG. 15 is also generated by the circuit of FIG. 16. The vertical position; i.e., the height; of the "gate", which constitutes a threshold level, is produced by the combined action of memory 206, converter 208 and amplifier 210 and is applied to the vertical (Y) deflection plates of the CRT. The operator selected values for the start and width of the "gate", entered by depressing key MO and the appropriate keys in group $T_3$ (FIG. 12), are used by microprocessor 62 to generate corresponding traversing times for the electron beam so that the beam may be intensity modulated in the manner required to place the "gate" bar at the correct position on the screen.

The ultrasonic test instrument described above is characterised by compact construction and ease of operation. The instrument may be assembled as a portable device capable of universal use. The internal computational and other features relieve the operator of many adjustments and calibrations which have previously been necessary when conducting non-destructive testing employing ultrasonic energy. A particularly advantageous feature of the present invention resides in the fact that the CRT screen, which is normally present for the display of echo signal information, is additionally utilized for the presentation of other information. This additional information includes both selected and computed data, the display of legends and dimensions of these data and displaying text and a monitor or time and amplitude "gate" bar signal which is commensurate with the region of interest within the body being examined. All of these additional displays may be presented at the same time as a display of the echo signal. The data entry keys on the control panel of the instrument are grouped in convenient fields related to function thereby further facilitating use and rendering possible a compact and practical construction.

While preferred embodiments have been shown and described, various modifications and substitutions may be made thereto without departing from the spirit and scope of the invention. Accordingly, it will be understood that the present invention has been described by way of illustration and not limitation.

What is claimed is:

1. Apparatus for displaying an echo related signal, said signal resulting from the reflection of ultrasonic energy from within an object being examined, the display apparatus comprising:

means for transducing the echo related signals into an information containing voltage signal;

cathode ray tube;

sweep voltage generator means, said sweep voltage generator means producing a sawtooth voltage for time-dependent deflection of the electron beam of the cathode ray tube in a first direction, said sawtooth voltage having preselected minimum and maximum levels and a predetermined slope;

means for applying the sawtooth voltage provided by said sweep voltage generator means to a first pair of deflection plates of said cathode ray tube;

data entry means for generating signals commensurate with a desired examination field in the test object in units of length and for generating signals commensurate with those parameters of the test object and ultrasound energy source which effect the transmission time of the ultrasonic energy from the source to the beginning of the desired examination field, said data entry means also generating signals commensurate with the parameters of a region within the examination field;

microprocessor means, said microprocessor means including means for storing information commensurate with signals generated by said data entry means, said microprocessor means computing and storing the delay time commensurate with the ultrasound energy transmission time between the source of ultrasonic energy and the depth in the test object commensurate with the beginning of the region within the examination field, said microprocessor further computing and storing the time commensurate with the length in the direction of ultrasound energy travel in the workpiece of the said region within the imaging field;

means responsive to the information computed and stored by said microprocessor means for generating deflection signals for application to a second pair of deflection plates of said cathode ray tube and for generating a cathode ray tube electron beam generating control signal;

means for selectively and alternately applying said information containing signals and said deflection signals generated in response to the information computed and stored by said microprocessor means to said cathode ray tube second pair of deflection plates; and means for applying said electron beam gating control signal to said cathode ray tube simultaneously with the application of said computed deflection signal whereby the bounds of the region and the echo related signals may be displayed.

2. The apparatus of claim 1 wherein said microprocessor means further computes from the entered signals a desired sawtooth voltage slope and stores said desired slope and wherein said apparatus comprises:

means responsive to the sawtooth voltage produced by said sweep voltage generator for producing and storing a signal commensurate with the actual slope of said sawtooth voltage;

means delivering said signal commensurate with actual slope to said microprocessor means, said microprocessor means generating a further output signal commensurate with the difference between the actual and desired sawtooth voltage slopes; and means commensurate with said signal commensurate with the difference in actual and desired slopes for varying the predetermined slope of the output waveform of said sweep voltage generator.

3. The apparatus of claim 2 further comprising:

a source of clock pulses; and wherein said means for measuring and storing a signal commensurate with actual sawtooth voltage slope comprises:

first counting circuit means responsive to the initiation and termination of the portion of the sawtooth voltage waveform having adjustable slope for counting the number of clock pulses which occur during traversal of the electron beam across the screen of said cathode ray tube in a first direction under the influence of said sawtooth voltage.

4. The apparatus of claim 3 further comprising:

means responsive to the delay time computed and stored by said microprocessor for generating a signal commensurate therewith; and second counting circuit means, said second counting circuit means being responsive to pulses derived from said clock pulse source and to the said signal commensurate with delay times, said second counting circuit means producing an initiation pulse for said sweep voltage generator means when the number of clock pulses received thereby corresponds to the computed delay time.

5. The apparatus of claim 4 wherein said means for generating deflection and gating signals in response to computed time includes:

means responsive to the signals commensurate with the beginning and length of the said region computed and stored by said microprocessor means for serially providing numerical signals commensurate with the onset and width of said region; and third counting circuit means, said third counting circuit means being responsive to clock pulses derived from said clock pulse source, said region onset and width signals being serially loaded into said third counter means whereby said third counter means will serially produce timing pulses commensurate with the onset and termination of said region.

6. The apparatus of claim 5 wherein said means for serially providing numerical visuals means includes:

a storage register for serially receiving and storing the values computed by said microprocessor means; and wherein said third counting circuit means comprises:

counter means connected to said storage register means; and bi-stable circuit means responsive to the timing pulses generated by said counter means for producing a square wave output signal having a duration commensurate with the width of the said region.

7. The apparatus of claim 6 further comprising:

means for selectively dividing the clock pulses delivered to said third counting circuit means counter.

8. The apparatus of claim 5 further comprising:

means responsive to said information containing signal and to said deflection and electron beam gating control signals generated in response to computed information for providing an indication that an information containing signal commensurate with a reflection from within the region exceeds a threshold level.

9. The apparatus of claim 8 wherein said microprocessor means computes from data entry means supplied signals a threshold level for the information containing signals and wherein said indication providing means comprises:

means responsive to the computed threshold for generating a signal commensurate therewith;

comparator means, said comparator means receiving the information containing signal and the signal commensurate with a threshold value, said comparator means providing an output signal when the amplitude of the information containing signal exceeds the threshold; and means responsive to an output signal provided by said comparator means for generating an alarm signal.

10. The apparatus of claim 9 wherein said applying means includes:

first switch means, said first switch means alternately applying said informational containing signal to said cathode ray tube second pair of deflection plates and applying said threshold signal to said second pair of deflection plates; and second switch means, said second switch means being operated in synchronism with said first switch means to apply the output of said third timing circuit means to the intensity control of said cathode ray tube simultaneously with application of said threshold signal to said deflection plates whereby the parameters of said region will be displayed as a bar on said cathode ray tube screen.

11. The apparatus of claim 10 wherein said means for serially providing numerical visuals means includes:

a storage register for serially receiving and storing the values computed by said microprocessor means; and wherein said third counting circuit means comprises:

counter means connected to said storage register means; and bi-stable circuit means responsive to the timing pulses generated by said counter means for producing a square wave output signal having a duration commensurate with the width of the said region.

12. The apparatus of claim 1 further comprising:

means responsive to said information containing signal and to said deflections and electron beam gating control signals generated in response to computed information for providing an indication that an information containing signal commensurate with a reflection from within the region exceeds a threshold level.

* * * * *